US007479500B2

(12) United States Patent
Webb et al.

(10) Patent No.: US 7,479,500 B2
(45) Date of Patent: Jan. 20, 2009

(54) ANTIDEPRESSANT PIPERIDINE DERIVATIVES OF HETEROCYCLEFUSED BENZODIOXANS

(75) Inventors: Michael Byron Webb, Levittown, PA (US); Gary Paul Stack, Ambler, PA (US); Magda Asselin, Mahwah, NJ (US); Deborah Ann Evrard, Hamilton Square, NJ (US)

(73) Assignee: Wyeth, Madison, NJ (US)

( * ) Notice: Subject to any disclaimer, the term of this patent is extended or adjusted under 35 U.S.C. 154(b) by 602 days.

(21) Appl. No.: 11/142,787

(22) Filed: Jun. 1, 2005

(65) Prior Publication Data
US 2005/0228009 A1 Oct. 13, 2005

Related U.S. Application Data

(62) Division of application No. 10/659,160, filed on Sep. 10, 2003, now Pat. No. 6,939,877.

(60) Provisional application No. 60/410,033, filed on Sep. 12, 2002.

(51) Int. Cl.
*A61K 31/44* (2006.01)
*C07D 413/14* (2006.01)
(52) U.S. Cl. .............. 514/338; 514/321; 514/324; 546/197; 546/202; 546/280.4; 546/282.4
(58) Field of Classification Search ........... 546/197, 546/202, 280.4, 282.4; 514/321, 324, 338
See application file for complete search history.

(56) References Cited

U.S. PATENT DOCUMENTS

| 5,276,042 | A | 1/1994 | Crenshaw et al. ........... 514/321 |
| 5,811,436 | A | 9/1998 | Leonard et al. ............. 514/321 |
| 6,218,405 | B1 | 4/2001 | Birch et al. ................ 514/321 |
| 6,593,350 | B2 * | 7/2003 | Stack et al. ................. 514/338 |
| 6,599,915 | B2 | 7/2003 | Tran et al. .................. 514/291 |
| 6,720,003 | B2 * | 4/2004 | Chen et al. .................. 424/464 |

FOREIGN PATENT DOCUMENTS

| EP | 0 151 826 A1 | 8/1985 |
| EP | 0 542 136 A1 | 5/1993 |
| FR | 2 103 639 A | 4/1972 |
| GB | 1354554 A | 6/1974 |
| WO | 91/13872 A1 | 9/1991 |
| WO | 92/09281 A2 | 6/1992 |
| WO | 94/01437 A1 | 1/1994 |
| WO | 95/07274 A1 | 3/1995 |
| WO | 98/16530 A1 | 4/1998 |
| WO | 98/40386 A1 | 9/1998 |

OTHER PUBLICATIONS

Blackburn et al. "Isosteric replacement . . ." Bioorg. Med. Chem. Lett. v. 5(22) p. 2589-2592 (1995).*
Loriga et al. "2-3-bis-4-fluorophenyl . . ." Bioorg. Med. chem. v.15, p. 3748-3755 (2007).*
Settimo et al. "Isosteric replacement of the . . ." Eur. J. Med. Chem. v.31, p. 951-956 (1996).*
Burkamp et al. "Novel and efficient . . ." CA 1999:145846 (1999).*
CA 131:237792, Heydorn "Paroxetine . . ." (1999).*
CA137:304164, Rosenberg "Selective seroronin . . ." (2002).*
CA137:353044, Stack et al. "Preparation of antidepressant . . ." (2002).*
CA139:332896, Tordera et al. "Effect of different . . ." (2003).*
Artigas, F., et al., "Pindolol induces a rapid improvement of depressed patients treated with serotonin reuptake inhibitors," *Arch Gen Psychiatry*, Mar. 1994, 51, 248-251.
Birch, A. M. et al., "N-Substituted (2,3-Dihydrox-1,4-benzodioxin-2-yl)methylamine Derivatives as $D_2$ Antagonists/5-$HT_{1A}$ Partial Agonists with Potential as Atypical Antipsychotic Agents," *J Med Chem*, 1999, 42, 3342-3355.
Blier, P., et al., "Effectiveness of pindolol with selected antidepressant drugs in the treatment of major depression," *J. of Clinical Psychopharmacology*, 1995, 15(3), 217-222.
Bundgaard, (Ed.), Design of Prodrugs, Elsevier, 1985.
Bundgaard, H., "Means to enhance penetration; Prodrugs as a means to improve the delivery of peptide drugs," *Advanced Drug Deliver Reviews*, 1992, 8, 1-38.
Bundgaard, *J. of Pharmaceutical Sciences*, 1988, 7(285 et seq.).
Cheetham, S.C., et al., "[$^3$H]paroxetine binding in rat frontal cortex strongly correlates with [$^3$H]5-HT uptake: effect of administration of various antidepressant treatments," *Neuropharmacol.*, 1993, 32(8), 737-743.
Eliel, E.L., Stereochemistry of Carbon Compounds, McGraw-Hill, NY, 1962.

(Continued)

*Primary Examiner*—Celia Chang
(74) *Attorney, Agent, or Firm*—Woodcock Washburn LLP

(57) ABSTRACT

Compounds of the Formula:

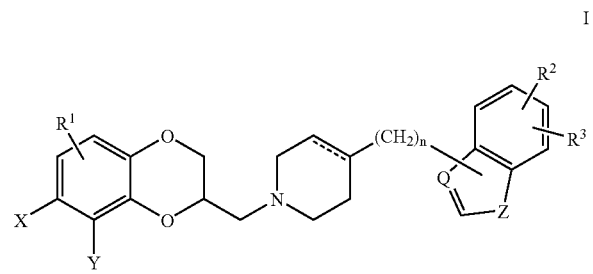

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction and related illnesses.

18 Claims, No Drawings

OTHER PUBLICATIONS

Higuchi, et al. (Eds.), Prodrugs as Novel Drug Delivery Systems, *American Chemical Society*, 1975.

Jacques, et al., Enantiomers, Racemates and Resolutions, *Wiley Interscience*, NY, 1981.

Krogsgaard-Larsen, et al. (Eds.), "Design and Application of Prodrugs," *Texbook of Drug Design and Development*, 1991, Chap. 5, 113-191.

Lazareno, S., et al., "Pharmacological characterization of acetylcholine-stimulated [$^3$S]-GTPγS binding mediated by human muscarinic m1-m4 receptors: antagonist studies," *Br. J. Pharmacol.*, 1993, 109, 1120-1127.

Ostrowski, S., "A synthesis of fused pyrimidine mono-n-oxides," Heterocycles, 1996, 43(2), p. 389-396.

Perez, V., et al., "Randomised, double-blind, placebo-controlled trial of pindolol in combination with fluoxetine antidepressant treatment," *The Lancet*,m May 31, 1997, 349, 1594-1597.

Remington's Pharmaceutical Sciences, 17$^{th}$ Ed., Gennaro, A.R. (Ed.), *Mack Publishing Company*, Easton, PA, 1985.

Tome, M.B., et al., "Serotonergic autoreceptor blocade in the reduction of antidepressant latency: personality variables and response to paroxetine and pindolol," *J. Affect Disord*, 1997, 44, 101-109.

Tome, M.B., et al., "Paroxetine and pindolol: a randomized trial of serotonergic antoreceptor blockade in the reduction of antidepressant latency," *Int. Clin. Psychopharmacol*, 1997, 12, 81-89.

Widder, et al. (Eds.), Methods in Enzymology, *Academic Press*, 1985, vol. 4.

Wilen, S.H., "Tables of Resolving Agents and Optical Resolutions," *Univ. of Notre Dame Press*, Notre Dame, IN, E.L. Eliel (Ed.), 1972, p. 268-298.

Wilen, S.H., et al., "Strategies in optical resolutions," *Tetrahedron*, 1977, 33, 2725-2736.

* cited by examiner

ANTIDEPRESSANT PIPERIDINE DERIVATIVES OF HETEROCYCLEFUSED BENZODIOXANS

CROSS-REFERENCE TO RELATED APPLICATIONS

This application is a divisional of U.S. application Ser. No. 10/659,160, filed Sep. 10, 2003, now U.S. Pat. No. 6,939,877 which claims the benefit of U.S. application Ser. No. 60/410,033, filed Sep. 12, 2002, the entire disclosures of which are incorporated herein by reference.

FIELD OF THE INVENTION

This invention relates to antidepressant piperidine derivatives of heterocycle-fused benzodioxans, to processes for preparing them, methods of using them and to pharmaceutical compositions containing them.

BACKGROUND OF THE INVENTION

Major depression is a serious health problem affecting more than 5% of the population, with a lifetime prevalence of 15-20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., The Lancet; 349:1594-1597 (1997)). Such a combination therapy would be expected to speed up the effect of the serotonin-reuptake-inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of Formula I:

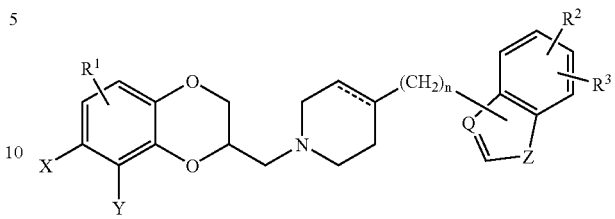

wherein
$R^1$, $R^2$ and $R^3$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

X and Y are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon. atoms, alkanamido of 2 to 6 carbon atoms, alkanesulfonyl of 1 to 6 carbon atoms or alkanesulfonamido of 1 to 6 carbon atoms, or X and Y, taken together, form —N=C($R^4$)—C($R^5$)=N—, —N=C($R^4$)—C($R^6$)=CH—, —N=C($R^4$)—N=CH—, —N=C($R^4$)—O—, —NH—C($R^7$)=N— or —NH—C($R^8$)=CH—;

$R^4$ and $R^5$ are, independently, hydrogen, halo, amino, mono- or di-alkylamino in which each alkyl group has 1 to 6 carbon atoms or alkyl of 1 to 6 carbon atoms;

$R^6$ is hydrogen or alkyl of 1 to 6 carbon atoms;

$R^7$ is hydrogen, halo, trifluoromethyl, pentafluoroethyl, amino, mono- or di-alkylamino in which each alkyl group has 1 to 6 carbon atoms or alkyl of 1 to 6 carbon atoms;

$R^8$ is hydrogen, halo, trifluoromethyl, pentafluoroethyl or alkyl of 1 to 6 carbon atoms;

the dotted line represents an optional double bond;

Z is oxygen or sulfur;

Q is carbon or nitrogen;

n is 0 or 1;

or a pharmaceutically acceptable salt thereof.

$R^1$ is preferably hydrogen, halo, cyano, trifluoromethyl, alkyl of 1 to 6 carbon atoms or alkoxy of 1 to 6 carbon atoms. More preferably, $R^1$ is hydrogen, halo or alkoxy of 1 to 6 carbon atoms. In still more preferred embodiments of the present invention, $R^1$ is hydrogen.

$R^2$ and $R^3$ are preferably independently selected from hydrogen, hydroxy, halo, cyano, carboxamido, alkyl of 1 to 6 carbon atoms, or alkoxy of 1 to 6 carbon atoms. In still more preferred embodiments of the present invention $R^2$ and $R^3$ are preferably independently selected from hydrogen, cyano or halogen.

$R^4$ and $R^5$ are preferably independently hydrogen, amino or alkyl of 1 to 6 carbon atoms. More preferably, $R^4$ and $R^5$ are independently hydrogen or alkyl of 1 to 3 carbon atoms.

$R^7$ and $R^8$ are preferably independently selected from hydrogen, trifluoromethyl, pentafluoroethyl or alkyl of 1 to 6 carbon atoms. More preferably, $R^7$ and $R^8$ are independently hydrogen, trifluoromethyl or alkyl of 1 to 3 carbon atoms.

$R^6$ is preferably hydrogen or alkyl of 1 to 3 carbon atoms, Z is preferably sulfur, Q is preferably carbon, n is preferably 0 and the dotted line represents a double bond.

In other preferred embodiments of the invention is provided compounds of Formula Ia.

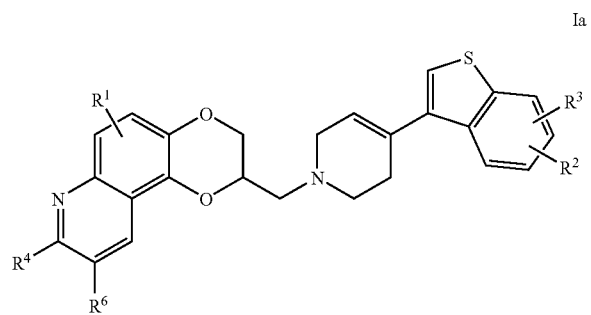

Ia wherein $R^1$, $R^2$, $R^3$, $R^4$ and $R^6$ are as described above.

In still other preferred embodiments of the invention is provided compounds of Formula Ib.

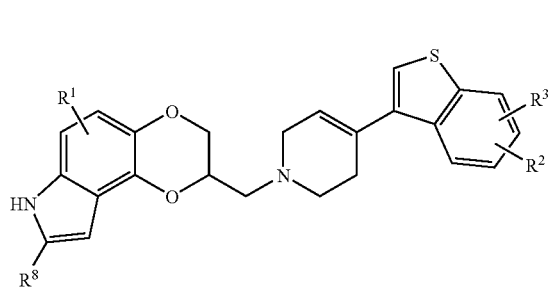

Ib wherein $R^1$, $R^2$, $R^3$ and $R^8$ are as described above.

This invention relates to both the R and S stereoisomers of the benzodioxan methylamines as well as to mixtures of the R and S stereoisomers. Throughout this application, the name of the product of this invention, where the absolute configuration of the compounds of the invention is not indicated is intended to embrace the individual R and S enantiomers as well as mixtures of the two. In some embodiments of the present invention the S enantiomer is preferred. For certain of the compounds of the invention (i.e., X and Y form an imidazole), tautomeric forms may exist. This application thus encompasses all tautomeric forms of compounds of the present invention.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared freed of the corresponding enantiomer. "Substantially free," as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

"Alkanamido," as used herein, refers to the group R—C(=O)—NH— where R is an alkyl group of 1 to 5 carbon atoms.

"Alkanoyl," as used herein, refers to the group R—C(=O)— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)$_2$—NH— where R is an alkyl group of 1 to 6 carbon atoms.

"Alkanesulfonyl," as used herein, refers to the group R—S(O)$_2$— where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH$_2$—C(=O)—.

"Carboalkoxy," as used herein, refers to the group R—O—C(=O)— where R is an alkyl group of 1 to 5 carbon atoms.

"Halogen" (or "halo"), as used herein, refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

2-(4-Benzo[b]thiophen-3-yl-3,6-dihydro-2H-pyridin-1-yl-methyl)-8-methyl-2,3-dihydro-[1,4]dioxino[2,3-f]quinoline;

2-(4-Benzo[b]thiophen-2-yl-3,6-dihydro-2H-pyridin-1-yl-methyl)-8-methyl-2,3-dihydro-[1,4]dioxino[2,3-f]quinoline;

2-[4-(5-Fluoro-benzo[b]thiophen-3-yl)-3,6-dihydro-2H-pyridin-1-ylmethyl]-8-methyl-2,3-dihydro-[1,4]dioxino[2,3-f]quinoline;

2-[4-(7-Methoxy-benzofuran-3-yl)-3,6-dihydro-2H-pyridin-1-ylmethyl]-8-methyl-2,3-dihydro-[1,4]dioxino[2,3-f]quinoline;

2-[4-(5-Fluoro-benzo[b]thiophen-3-yl)-3,6-dihydro-2H-pyridin-1-ylmethyl]-2,3-dihydro-[1,4]dioxino[2,3-f]quinoline;

2-(4-Benzo[b]thiophen-3-yl-3,6-dihydro-2H-pyridin-1-yl-methyl)-2,3-dihydro-[1,4]dioxino[2,3-f]quinoline;

2-(4-Benzo[b]thiophen-3-yl-3,6-dihydro-2H-pyridin-1-yl-methyl)-2,3-dihydro-7H-[1,4]dioxino[2,3-e]indole;

2-[4-(5-Fluoro-benzo[b]thiophen-3-yl)-3,6-dihydro-2H-pyridin-1-ylmethyl]-2,3-dihydro-7H-[1,4]dioxino[2,3-e]indole;

8-(4-Benzo[b]thiophen-3-yl-3,6-dihydro-2H-pyridin-1-yl-methyl )-2-methyl-7,8-d dihydro-[1,4]dioxino[2,3-g][,3]benzoxazole;

2-(4-Benzo[b]thiophen-7-yl-3,6-dihydro-2H-pyridin-1-yl-methyl)-8-methyl-2,3-dihydro-[1,4]dioxino[2,3-f]quinoline;

2-(4-Benzofuran-2-yl-3,6-dihydro-2H-pyridin-1-ylmethyl)-8-methyl-2,3-dihydro-[1,4]dioxino[2,3-f]quinoline;

2-(4-Benzofuran-2-yl-piperidin-1-ylmethyl)-8-methyl-2,3-dihydro-[1,4]dioxino[2,3-f]quinoline;

2-[4-(5-Chloro-benzo[b]thiophen-3-yl)-3,6-dihydro-2H-pyridin-1-ylmethyl]-8-methyl-2,3-dihydro-[1,4]dioxino[2,3-f]quinoline;

2-(4-Benzoxazol-2-yl-piperidin-1-ylmethyl)-8-methyl-2,3-dihydro-[1,4]dioxino[2,3-f]quinoline;

Compounds of the present invention are prepared in accordance with the following general description and specific examples. Variables used are as defined for Formula I, unless otherwise noted. Specifically (Scheme 1), the appropriately substituted piperidine (2) is combined with a suitably substituted benzodioxan methyltosylate or bromide (1) in a solvent such as dimethyl sulfoxide and heated to a temperature of 70-100° C. for several hours as illustrated below. Alternatively, the appropriately substituted piperidine may be acylated with a suitably substituted benzodioxan carboxylic acid chloride, and the resulting amide reduced to the amine with a suitable reducing agent such as lithium aluminum hydride or borane/THF. The piperidine may also be combined with a suitably substituted benzodioxan carboxaldehyde in the presence of a reducing agent such as sodium cyanoborohydride.

Scheme 1

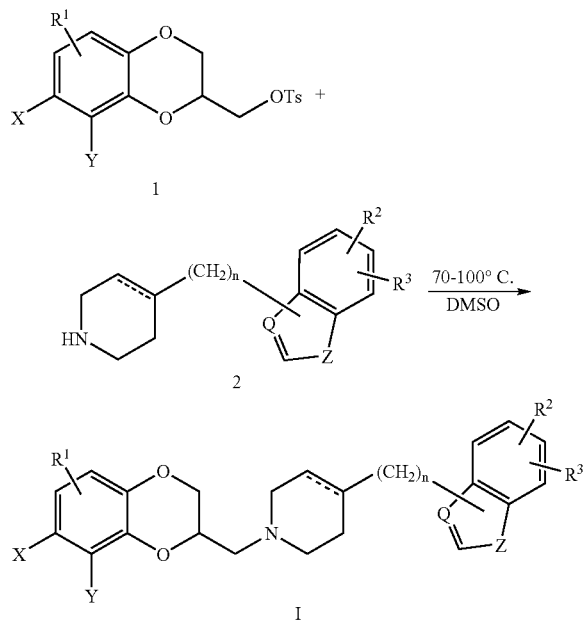

Alternatively (Scheme 2), an appropriately substituted pyridine (3) may be alkylated with a suitably substituted benzodioxan methyltosylate or bromide (1) by heating the mixture in a high-boiling polar solvent such as dimethyl sulfoxide to produce the pyridinium ion (4). The pyridinium ion may be reduced to the tetrahydropyridine by treatment with a suitable reducing agent such as sodium borohydride in ethanol or directly to the piperidine by treatment with hydrogen over a suitable catalyst such as palladium on carbon.

Scheme 2

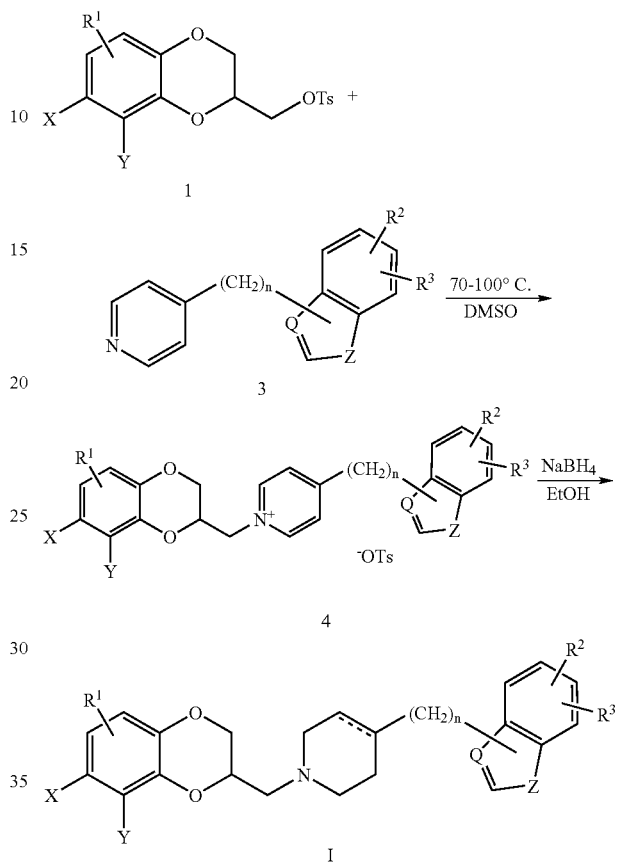

The benzodioxan methyltosylates and halides (1) are known compounds or they may be prepared from the appropriately substituted salicylaldehydes by the method (a) described in Scheme 3 below. The salicylaldehyde (5) is alkylated with an epihalohydrin or glycidyl arylsulfonate in the presence of a suitable base. The aldehyde moiety is then converted to a phenol by a Baeyer-Villager procedure and cyclization to the benzodioxan methanol (7) effected by treatment with a base such as potassium carbonate. The alcohol is elaborated to a tosylate (1) by treatment with p-toluenesulfonyl chloride and a tertiary amine base or to a bromide by treatment. Alternatively (b), the substituted salicylaldehyde (8) may be protected with a suitable protecting group such as benzyl and the aldehyde (9) converted to a phenol (10) as described above. Following elaboration of the phenol to the glycidyl ether (11) by treatment with an epihalohydrin or glycidyl arylsulfonate, deprotection and cyclization are effected in a single step via a transfer hydrogenation in the presence of sodium bicarbonate. The bromide or tosylate is prepared as described above. Or the benzodioxan methylbromide may be prepared from a suitably substituted guaiacol (12) by procedure (c) shown above. The guiacol is alkylated with a glycidyl arylsulfonate or an epihalohydrin as described above. The methyl ether (13) is then cleaved by treatment with 48% HBr; this also converts the epoxide to a bromohydrin (14). Cyclization directly to the benzodioxan methylbromide (1) is effected by the Mitsonobu procedure.

Scheme 3

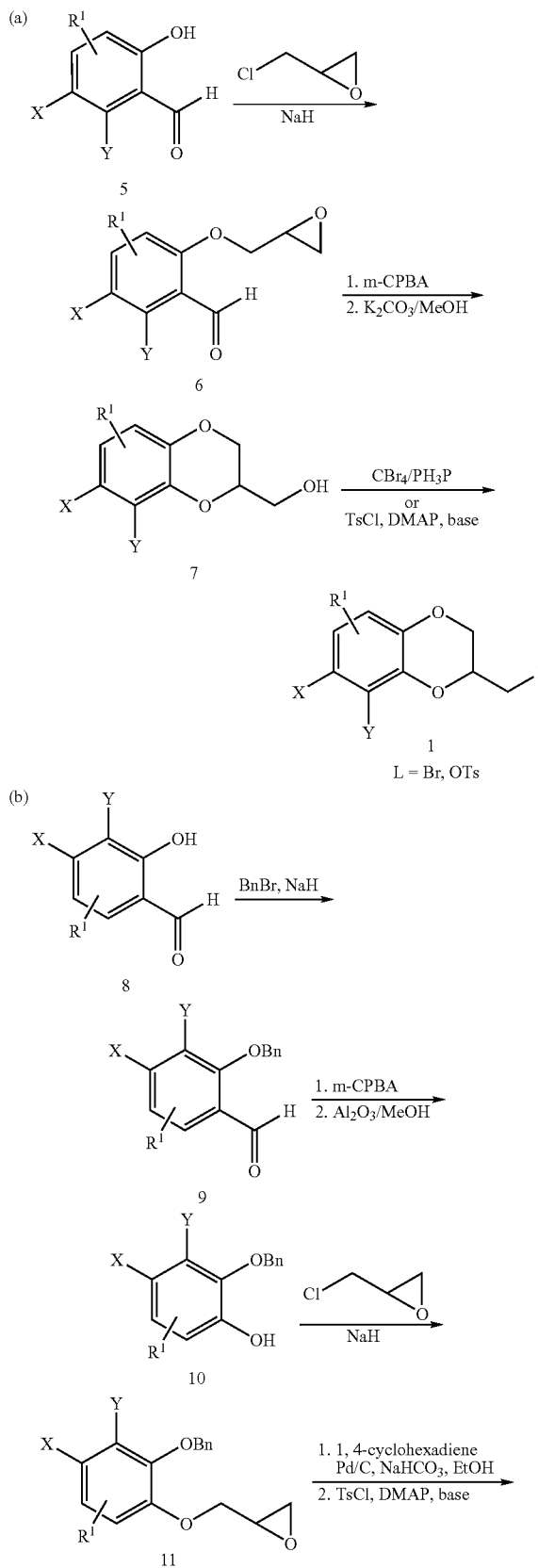

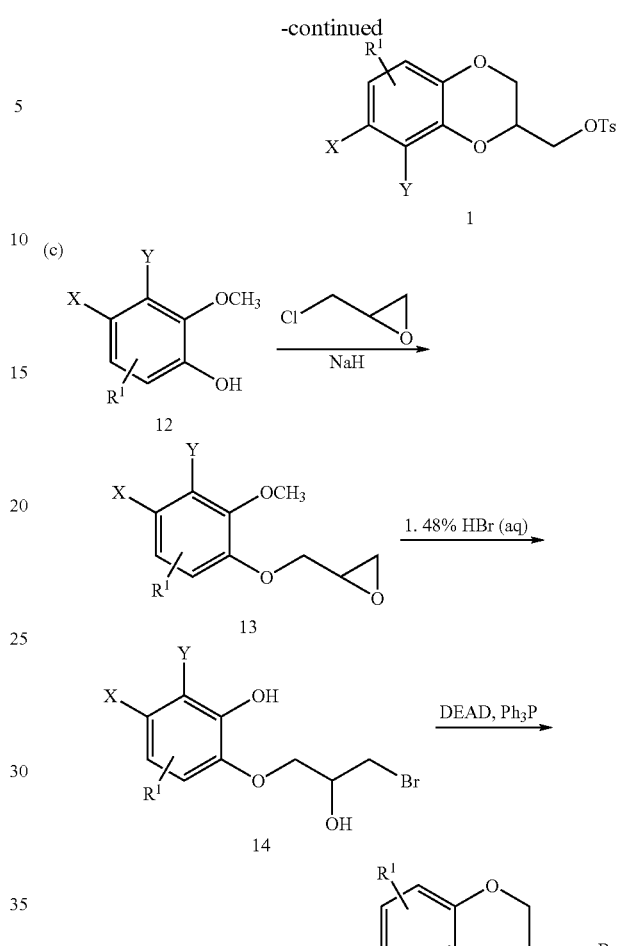

The 2,3-dihydro-1,4-dioxino[2,3-f]quinolin-2-ylmethylamines of the invention in which $R^4$ is H are alternatively prepared as illustrated in Scheme 4 below. Specifically, the appropriately substituted nitroguaiacol (15) is alkylated with allyl bromide in the presence of a suitable base such as sodium hydride and then demethylated by a reagent such as sodium hydroxide. The resulting 4-nitro-2-allyloxyphenol (17) is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol (19) is converted to the tosylate by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene. Allylic oxidation of 20 with selenium dioxide in refluxing dioxane/water gives the o-nitrocinnamaldehyde, which upon reduction with iron in acetic acid cyclizes to the 2,3-dihydro-1,4-dioxino[2,3-f] quinoline-2-methyltosylate (21) or halide. Replacement of the tosylate or halide with the appropriately substituted piperidine in some high boiling solvent such as dimethyl sulfoxide gives the title compounds of the invention.

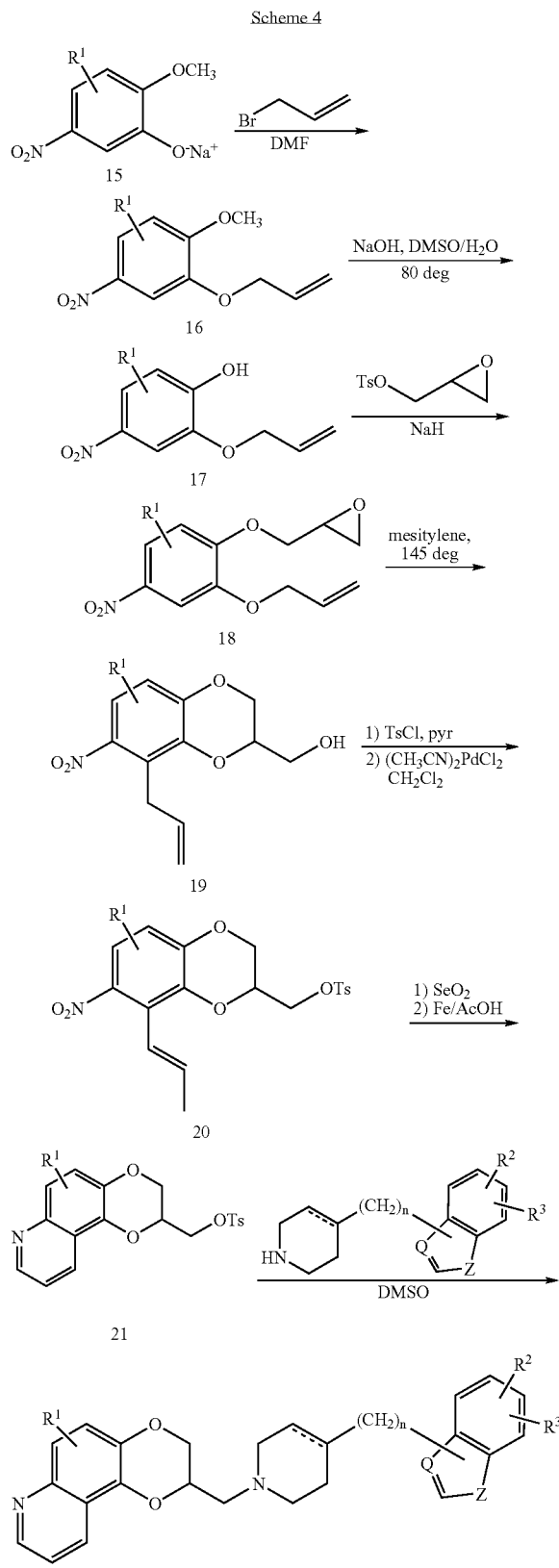

The 2,3-dihydro-1,4-dioxino[2,3-f]quinolin-2-ylmethylamines of the invention in which $R^4$ is alkyl may be prepared from the nitro olefin described above in the following manner (Scheme 5). The rearranged olefin (20) is treated sequentially with ozone and a tertiary amine or with osmium tetroxide and sodium periodate to give the o-nitrobenzaldehyde (22). Condensation with the appropriate triphenylphosphorylidene ketone under Wittig conditions gives the o-nitrocinnamyl ketone (23), which upon reduction by iron in acetic acid, cyclizes to the corresponding 2,3-dihydro-1,4-dioxino[2,3-f] quinoline-2-methyltosylate (24). Replacement of the tosylate with the appropriately substituted piperidine as above gives the title compounds of the invention. Substitution of trimethyl phosphonoacetate for the triphenylphosphorylidene ketone in the Wittig procedure above, followed by reduction of the nitro group with tin (II) chloride and cyclization in acid gives the compounds of the invention in which $R^4$ is hydroxy. Treatment of the hydroxy derivative with an inorganic acid chloride such as phosphoryl chloride or bromide gives the compounds of the invention in which $R^4$ is halo. Substitution of diethyl cyanomethylphosphonate for the triphenylphosphorylidene ketone in the Wittig procedure above, followed by reduction of the nitro group with tin (II) chloride and cyclization in acid gives the compounds of the invention in which $R^4$ is amino.

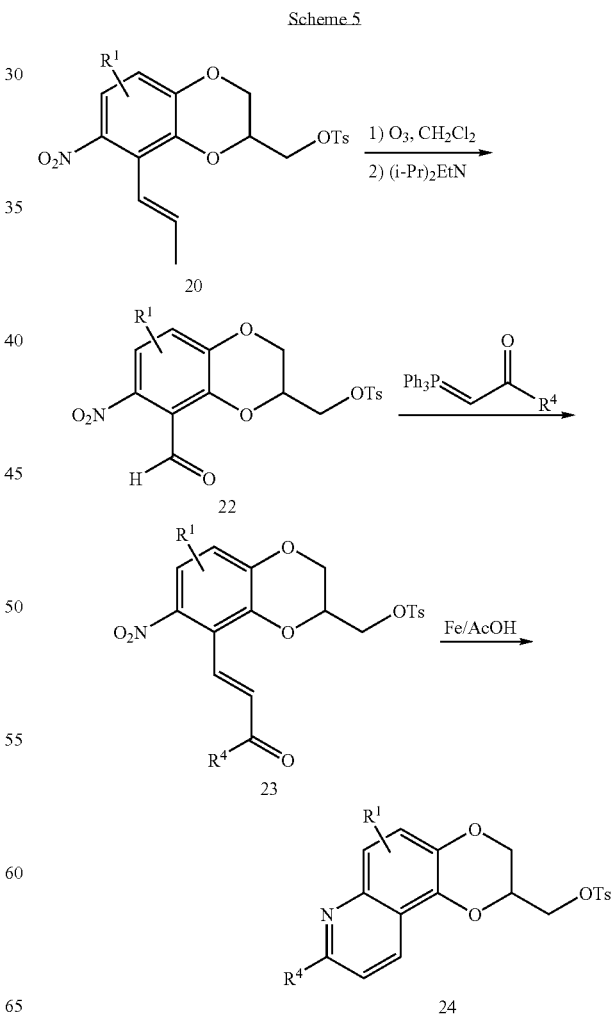

Compounds of the invention in which R¹ is attached to position 6 of the 2,3-dihydro-1,4-dioxino[2,3-f]quinolin-2-ylmethylamines may be alternatively prepared by a variation of the Skraup quinoline synthesis according to Scheme 6 below. The appropriately substituted benzodioxan methyltosylate (25) is nitrated under standard conditions with nitric acid in a solvent such as dichloroethane and the resulting nitro compound (26) reduced by treatment with hydrogen in the presence of a catalyst such as platinum on sulfide carbon. Treatment of the resulting aniline (27) with acrolein in the presence of hydrogen chloride and an oxidant such as p-chloranil or naphthoquinone gives the corresponding 2,3-dihydro-1,4-dioxino[2,3-f]quinoline (28). Replacement of the tosylate with the appropriately substituted piperidine as above gives the title compounds of the invention.

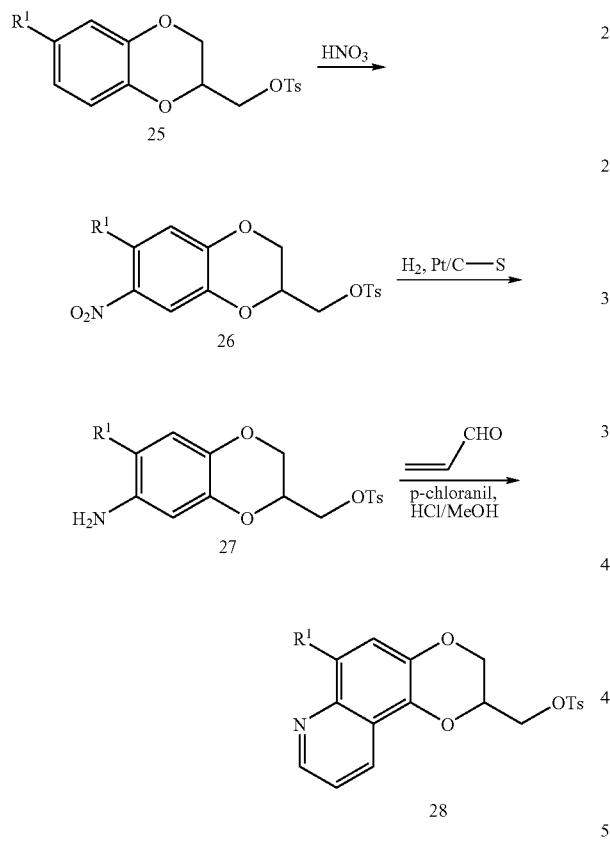

The 2,3-dihydro-1,4-dioxino[2,3-f]quinazolin-2-ylmethylamines of the invention are prepared as illustrated below (Scheme 7). The o-nitrobenzaldehyde (22) described above is converted to the oxime (29) by treatment with hydroxylamine hydrochloride in the presence of a suitable base such as sodium acetate and the nitro group reduced to the amine by hydrogenation over palladium on carbon. Cyclization to the quinazoline-N-oxide is effected by treatment at reflux with the appropriate ortho ester according to the method of Ostrowski (*Heterocycles*, vol. 43, No. 2, p. 389, 1996). The quinazoline N-oxide may be reduced to the quinazoline (30) by a suitable reducing agent such as hydrogen over Raney-nickel. Alternatively, an extended period of reflux in the ortho ester gives the reduced quinazoline directly via a dispropor-tionation reaction and the 2,3-dihydro-1,4-dioxino[2,3-f]quinazoline-2-methyltosylate or halide may be isolated by column chromatography. Replacement of the tosylate or halide with the appropriately substituted piperidine in some high boiling solvent such as dimethyl sulfoxide gives the title compounds of the invention.

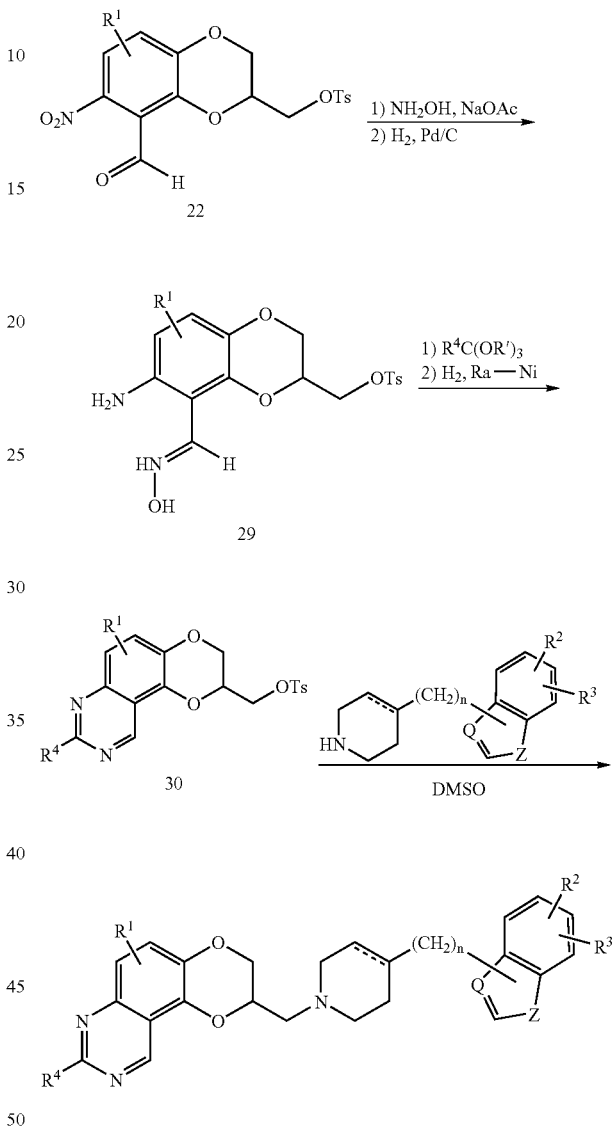

The 2,3-dihydro-1,4-dioxino[2,3-f]quinazolin-2-ylmethylamines of the invention may be alternatively prepared from the rearranged olefin described above by the method outlined in Scheme 8 below. The nitro olefin (20) is first reduced to the aniline by treatment with a suitable reducing agent such as stannous chloride dihydrate in refluxing ethyl acetate and the resulting amine acylated with the appropriate acyl halide or anhydride. The olefin (31) is then converted to the aldehyde (32) by cleavage with catalytic osmium tetroxide in the presence of excess sodium periodate. Cyclization directly to the 2,3-dihydro-1,4-dioxino[2,3-f]quinazoline-2-methyltosylate (30) or halide is effected by treatment of the amido aldehyde (32) with ammonia and replacement of the tosylate or halide with the appropriately substituted piperidine in some high boiling solvent such as dimethyl sulfoxide as described above gives the title compounds of the invention.

Scheme 8

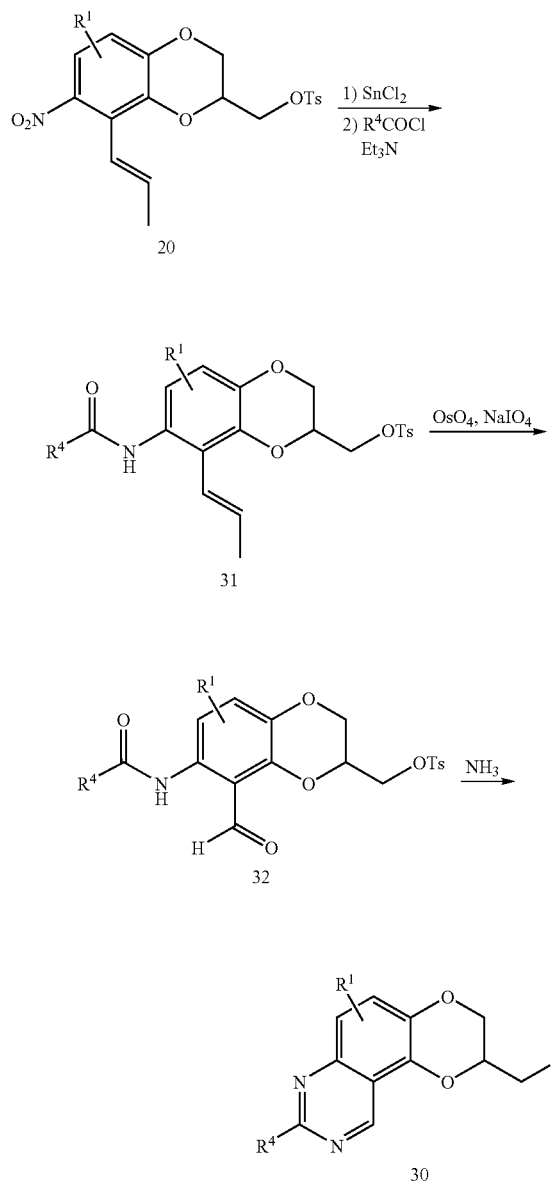

Scheme 9

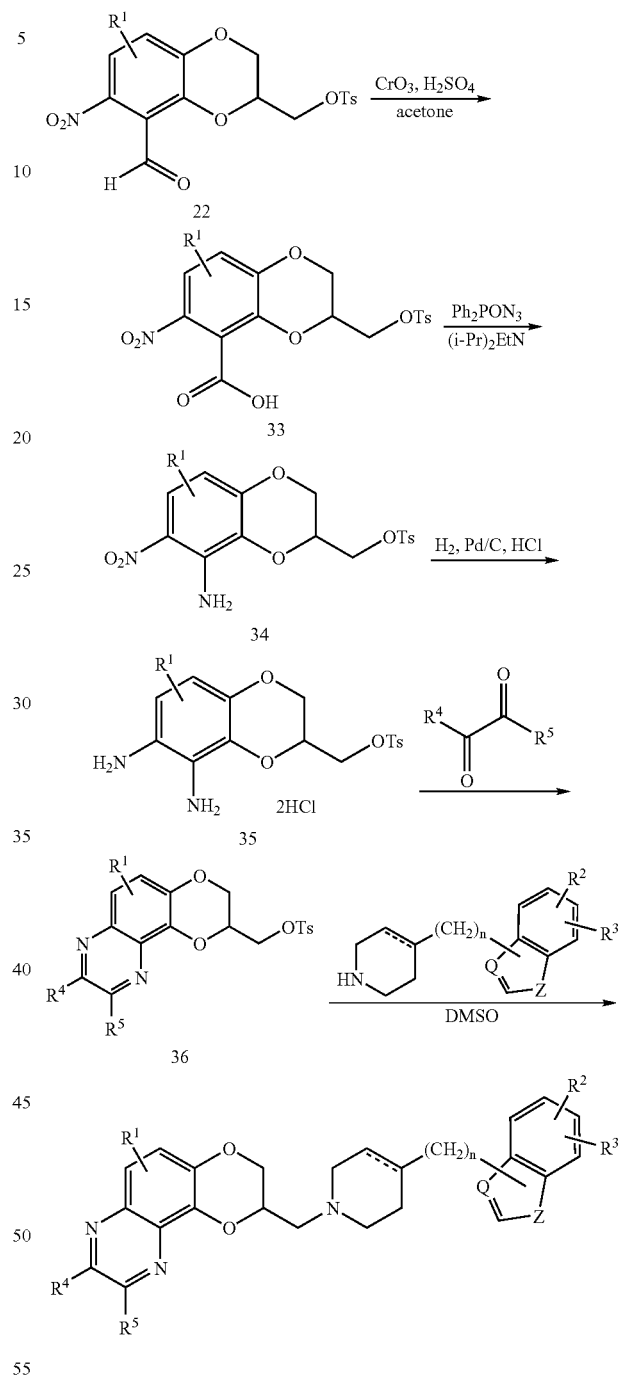

The 2,3-dihydro-1,4-dioxino[2,3-f]quinoxalin-2-ylmethylamines of the invention are prepared as illustrated in Scheme 9 below. The o-nitrobenzaldehyde (22) described above is oxidized to the o-nitrobenzoic acid (33) by a suitable oxidant such as chromium trioxide (Jones' oxidation) or sodium chlorite and the acid converted to the o-nitroaniline (34) with diphenylphosphoryl azide (DPPA) in the presence of a tertiary base such as diisopropylethylamine. Reduction of the resulting nitroaniline to the diamine (35) with hydrogen and palladium on carbon and cyclization by treatment with the appropriate dicarbonyl compound (for example, glyoxal, 2,3-butanedione, 3,4-hexanedione) gives the 2,3-dihydro-1,4-dioxino[2,3-f]quinoxaline-2-methyltosylate (36) or halide. Replacement of the tosylate or halide with the appropriately substituted piperidine in some high boiling solvent such as dimethyl sulfoxide gives the title compounds of the invention.

The o-nitrobenzaldehyde (22) used in the chemistry described above may be alternatively prepared as shown in scheme 10 below. The appropriate mono allylated catechol (37) is elaborated with glycidyl tosylate as described above and rearranged in refluxing mesitylene. Cyclization to the benzodioxan methanol (39) is effected by treatment with sodium bicarbonate in ethanol and the alcohol is converted to the tosylate (40) or halide as described above. After rearrangement of the double bond by treatment with catalytic bis-acetonitrile palladium (II) chloride in refluxing methylene chloride and cleavage with ozone or osmium tetroxide/ sodium periodate as described above, the resulting aldehyde (41) is regioselectively nitrated with a combination of nitric acid and tin (IV) chloride.

sulfonic acid. Replacement of the tosylate or halide with the appropriately substituted piperidine in some high boiling solvent such as dimethyl sulfoxide gives the title compounds of the invention.

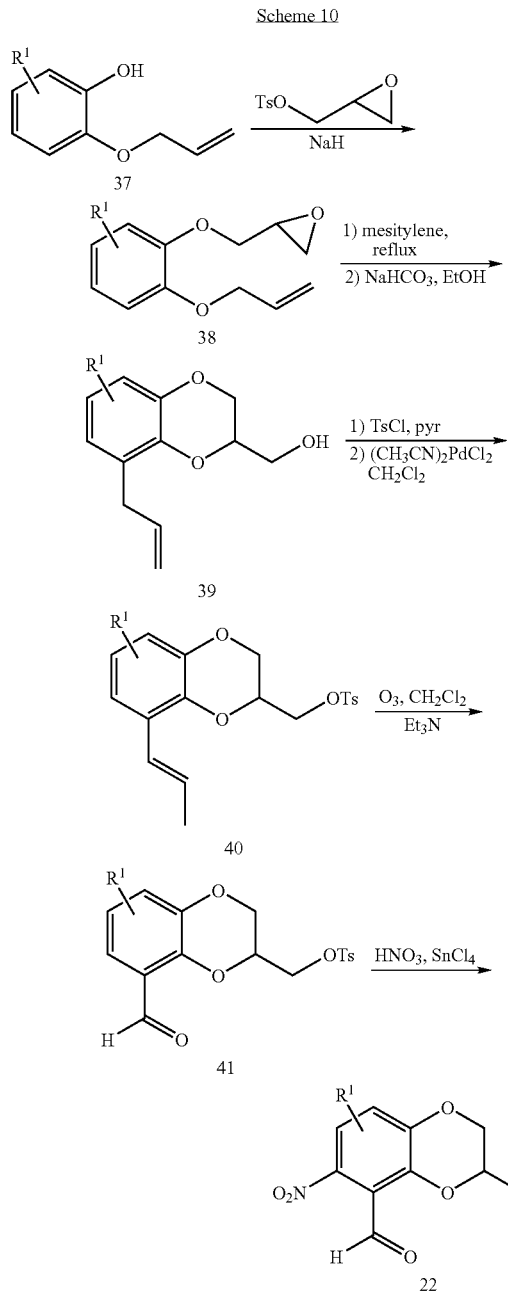

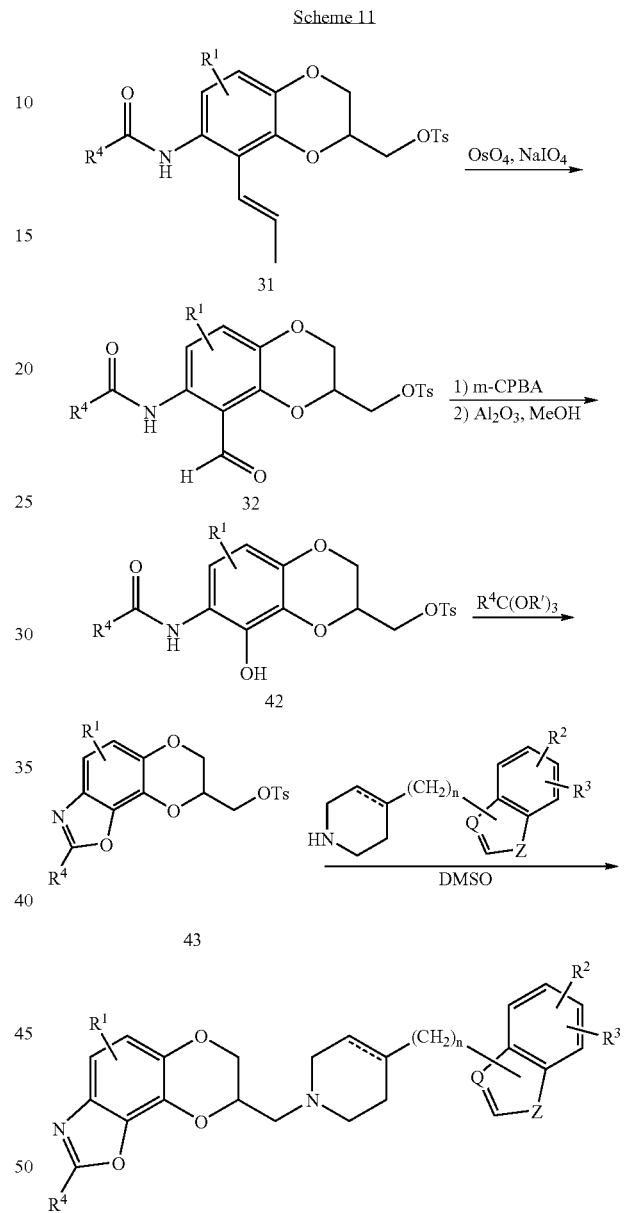

The 7,8-dihydro[1,4]dioxino[2,3-g][1,3]benzoxazol-8-yl-methylamines of the invention are prepared as illustrated in Scheme 8 below. The amido olefin (31) described in Scheme 8 is cleaved to the corresponding o-amidobenzaldehyde (32) by treatment with catalytic osmium tetroxide in the presence of sodium periodate. The aldehyde is converted to the phenol (42) by treatment with meta-chloroperoxybenzoic acid in a Baeyer-Villager reaction and cyclization to the 7,8-dihydro [1,4]dioxino[2,3-g][1,3]benzoxazole (43) is effected by treatment at reflux with an appropriate dehydrating agent such as an ortho ester or an acid catalyst such as p-toluene- Alternatively (Scheme 12), the nitro olefin (20) may be reduced with tin (II) chloride as described in Scheme 8 above and protected with a suitable protecting group such as carbobenzoxy (Cbz) before the olefin is cleaved to the aldehyde (45) by treatment with osmium tetroxide/sodium periodate and the aldehyde converted to a phenol (46) by the Baeyer-Villager procedure. Deprotection by treatment with hydrogen over palladium on carbon gives the o-aminophenol, (47) which is cyclized to the 7,8-dihydro[1,4]dioxino[2,3-g][1,3] benzoxazole (43) by treatment with the appropriate ortho ester, carboxylic acid or anhydride. Treatment of the o-aminophenol with cyanogen bromide or chloride or a suitably substituted carbamoyl chloride leads to compounds of the invention in which $R^4$ is amino. Treatment of the o-aminophenol with carbonyl diimidazole gives the oxazolone that leads to compounds of the invention in which $R^4$ is halo via treatment with an inorganic anhydride such as phosphoryl chloride or bromide. Replacement of the tosylate with the appropriately substituted piperidine as above gives the title compounds of the invention.

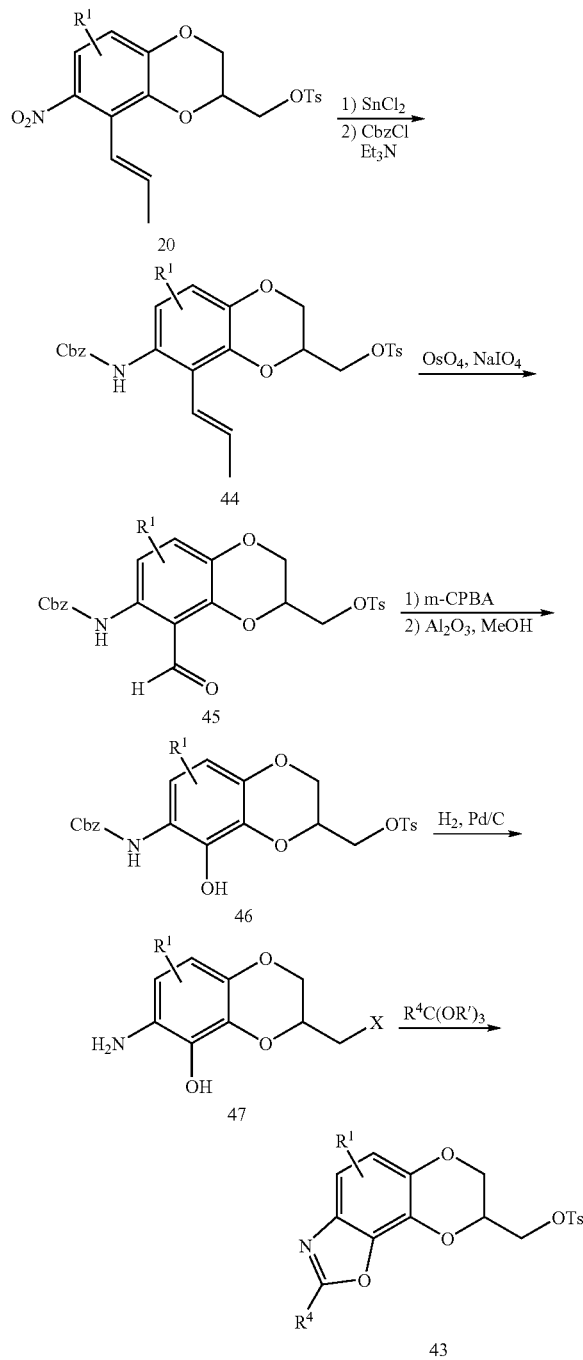

Compounds of the invention in which $R^1$ is hydrogen and $R^4$ is alkyl are most conveniently prepared according to scheme 13 below. The appropriate 2',3',4'-trihydroxyacylphenone (48) is regioselectively alkylated with glycidyl tosylate or an epihalohydrin in the presence of a base such as sodium carbonate to give the corresponding 7-acyl-8-hydroxybenzodioxan-2-methanol (49). Following conversion of the ketone to the oxime (50) by reaction with hydroxylamine hydrochloride and sodium acetate, cyclization to the oxazole (51) is effected by treatment with phosphoryl chloride in the appropriate dimethylalkanoic acid amide. The resulting 7,8-dihydro-1,6,9-trioxa-3-aza-cyclopenta[a]naphthalene-8-methanol is converted to the tosylate (52) by treatment with p-toluenesulfonyl chloride in pyridine and combined with the appropriate piperidine as described above to give the title compounds of the invention.

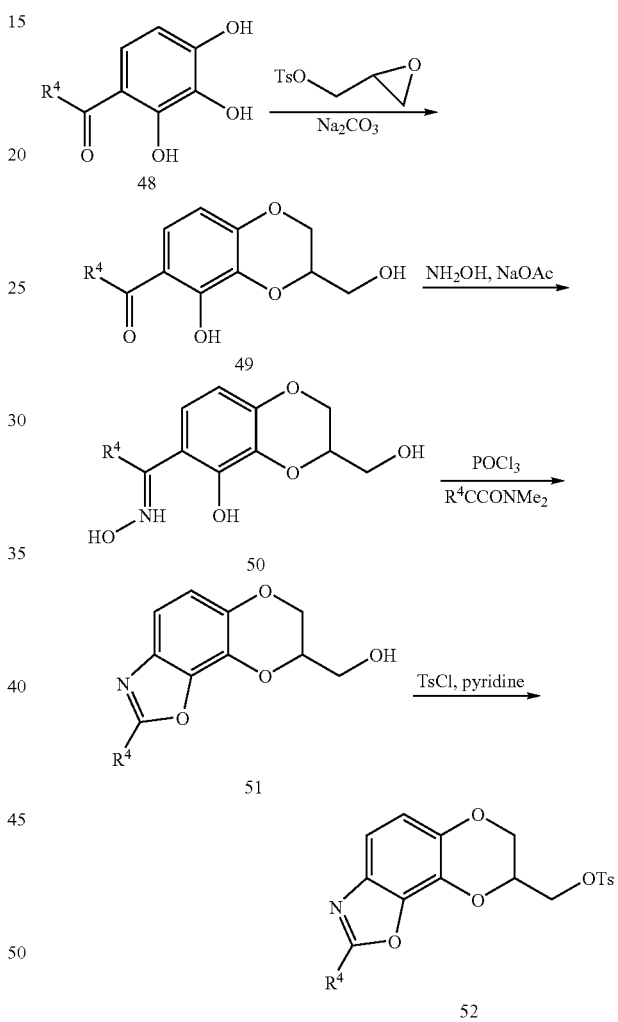

The 7,8-dihydro-3H-6,9-dioxa-1,3-diaza-cyclopenta[a] naphthalenes of the invention are prepared as illustrated in Scheme 14 below. The diamine 35 described in Scheme 9 is cyclized by treatment at reflux with the appropriate carboxylic acid to give the imidazole (53). Refluxing the diamine dihydrochloride in higher boiling carboxylic acids occasionally causes replacement of a tosylate group with a chloride. Replacement of the tosylate or halide with the appropriately substituted piperidine in some high boiling solvent such as dimethyl sulfoxide gives the 7,8-dihydro-3H-6,9-dioxa-1,3-diaza-cyclopenta[a]naphthalenes of the invention in which $R^7$ is hydrogen, perfluoroalkyl or alkyl. Treatment of the diamine described above with cyanogen bromide or chloride or a suitably substituted carbamoyl chloride leads to compounds of the invention in which $R^7$ is amino. Treatment of the diamine with carbonyl diimidazole gives the imidazolone which leads to compounds of the invention in which $R^7$ is halo via treatment with an inorganic anhydride such as phosphoryl chloride or bromide. Replacement of the tosylate with the appropriately substituted piperidine as above gives the title compounds of the invention.

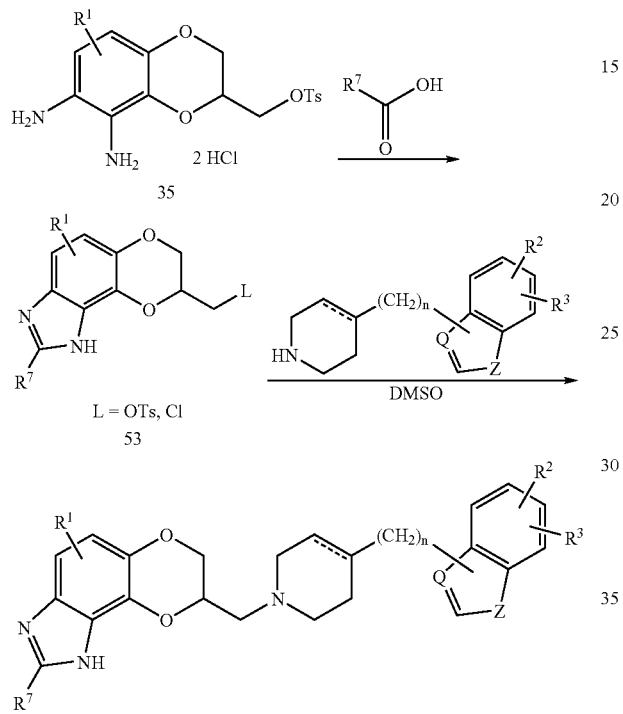

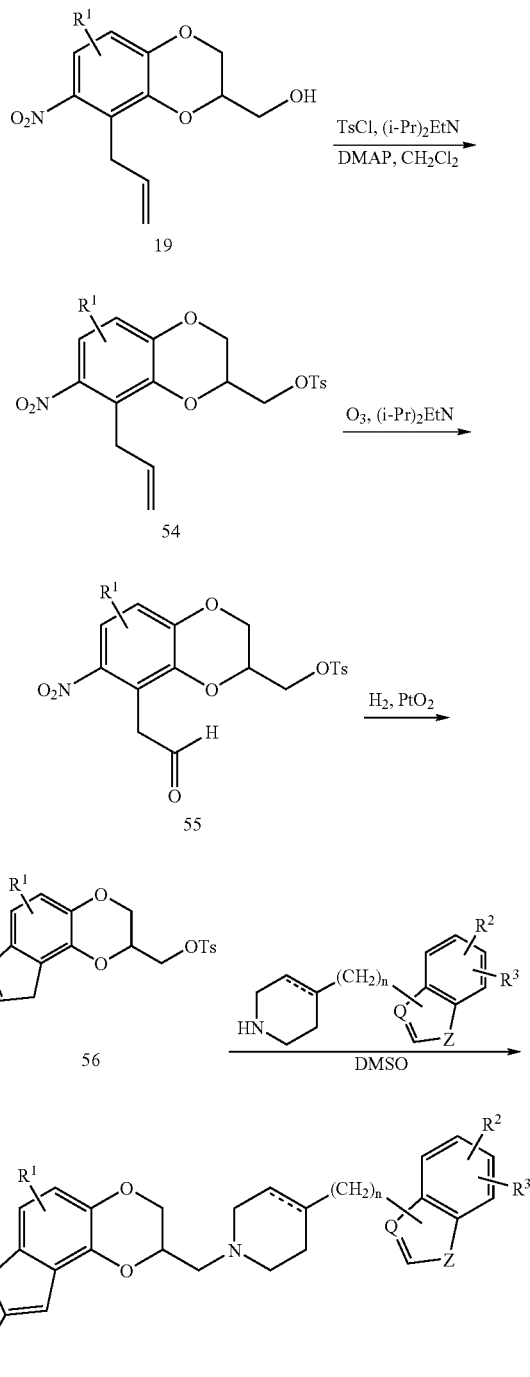

The 2,3-dihydro-7H-[1,4]dioxino[2,3-e]indoles of the invention are prepared. as illustrated in Scheme 15 below. Specifically, the primary alcohol (19) from the Claisen rearrangement described in Scheme 4 is converted to the tosylate (54) by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then cleaved to the aldehyde (55) by treatment with ozone at low temperature, followed by work-up with a tertiary base such as diisopropylethylamine or triethylamine, or by treatment with catalytic osmium tetroxide and sodium periodate. Reduction of the nitro group with hydrogen over platinum oxide leads directly to formation of the indole (56) in which $R^8$ is hydrogen. Alternatively, the aldehyde may be treated with an appropriate alkyl Grignard reagent or with trifluoromethyl trimethylsilane in the presence of cesium fluoride, then oxidized to a ketone with a suitable oxidant such as pyridinium chlorochromate (PCC) or the Swern reagent and reduced with hydrogen over platinum oxide to give the indoles in which $R^8$ is alkyl or trifluoromethyl. Replacement of the tosylate or halide with the appropriately substituted piperidine in some high boiling solvent such as dimethyl sulfoxide gives the title compounds of the invention.

The 2,3-dihydro-7H-[1,4]dioxino[2,3-e]indoles of the invention may alternatively be prepared from nitroaldehyde 21 by the following procedure (Scheme 16). The o-nitrobenzaldehyde (22) is condensed with the appropriate nitroalkane in the presence of a suitable base catalyst to yield the corresponding o,β-dinitrostyrene (57). Reduction of both nitro groups with hydrogen over palladium on carbon is accompanied by cyclization to form the indole (58). Replacement of the tosylate with the appropriately substituted piperidine as above gives the title compounds of the invention.

Scheme 16

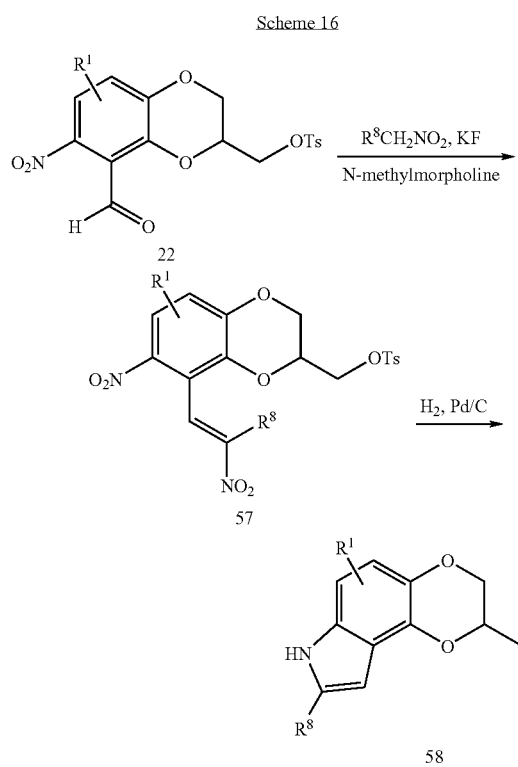

The compounds of the invention may be resolved into their enantiomers by conventional methods or, preferably, the individual enantiomers may be prepared directly by substitution of (2R)-(−)-glycidyl 3-nitrobenzene-sulfonate or tosylate (for the S benzodioxan methanamine) or (2S)-(+)-glycidyl 3-nitrobenzene-sulfonate or tosylate (for the R enantiomer) in place of epihalohydrin or racemic glycidyl tosylate in the procedures above.

In yet another method, the heterocycle-fused benzodioxans of the present invention may be prepared in accordance with Scheme 17. The synthesis of compound I is comprised of steps that begin with halogenation of 59 where R' is alkyl of 1-6 carbon atoms, with reagents such as N-halosuccinimide in acetonitrile to give 60 (where Hal is halogen such as Br, Cl or I). Deprotecting 60 with Lewis acids such as boron tribromide, boron trichloride, aluminum trichloride, ferric chloride, or trimethylsilyl iodide in a suitable solvent such as methylene chloride, or with strong protic acids such as HBr and HCl gives the salt 61. Free base 61 may be obtained by neutralization with an Amberlyst A-21 resin slurry in polar solvents such as ethanol or methanol.

Alkylation of 61, either as the free base or as the salt, with benzyl or substituted benzyl protected glycidyl ethers

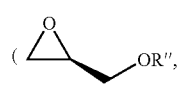

where R″ is benzyl, substituted benzyl such as 4-bromobenzyl, 3,4-dimethoxybenzyl, 2- or 4-nitrobenzyl, or 4-methoxybenzyl) in suitable polar solvents such as DMSO, DMF, or DMA in the presence of bases such as sodium carbonate, potassium carbonate, or triethylamine gives 62. 62 was then cyclized using palladium catalysts such as tris(dibenzylideneacetone)dipalladium, tetrakis(triphenylphosphine)palladium, or palladium acetate with ligands from the group consisting of (±) BINAP and separate enantiomers thereof, (±) Tol-BINAP and separate enantiomers thereof; 1-1'-bis(diphenylphosphino) ferrocene, 1,3-bis(diphenylphosphino)propane, and 1,2 bis(diphenyl-phosphino)ethane in the presence of bases such as NaH, LiH, KH, potassium carbonate, sodium carbonate, titanium carbonate, cesium carbonate, potassium t-butoxide or potassium phosphate tribasic in suitable solvent such as toluene, or alternatively, with copper catalyst such as copper iodide in the presence of bases such NaH, LiH, KH in a suitable solvent such as toluene to afford 63.

Scheme 17

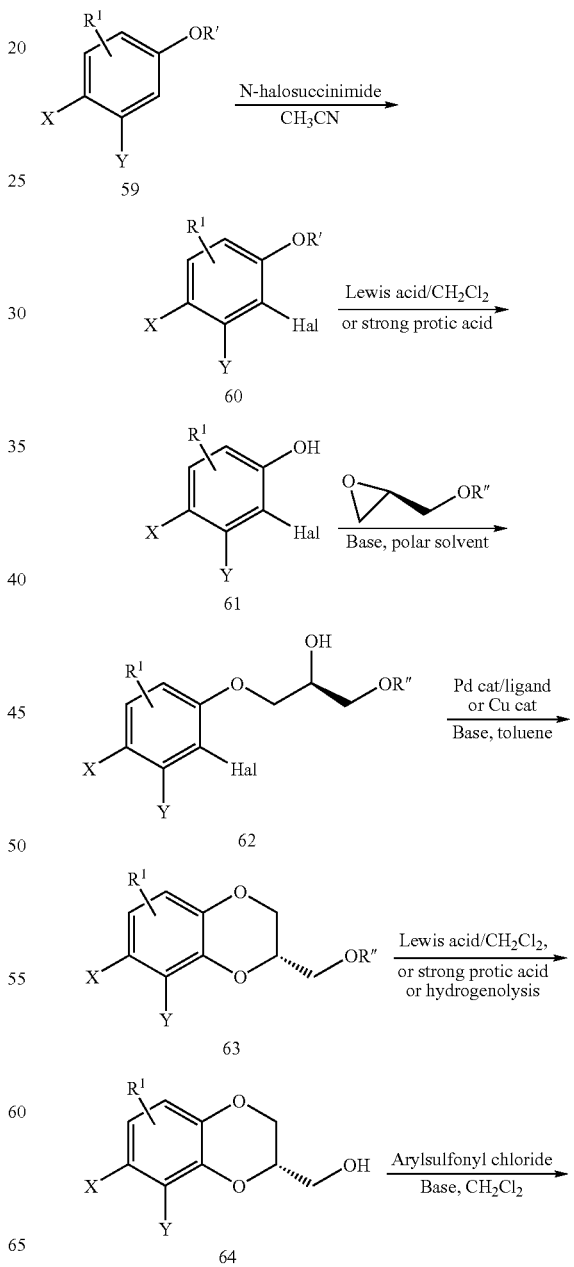

-continued

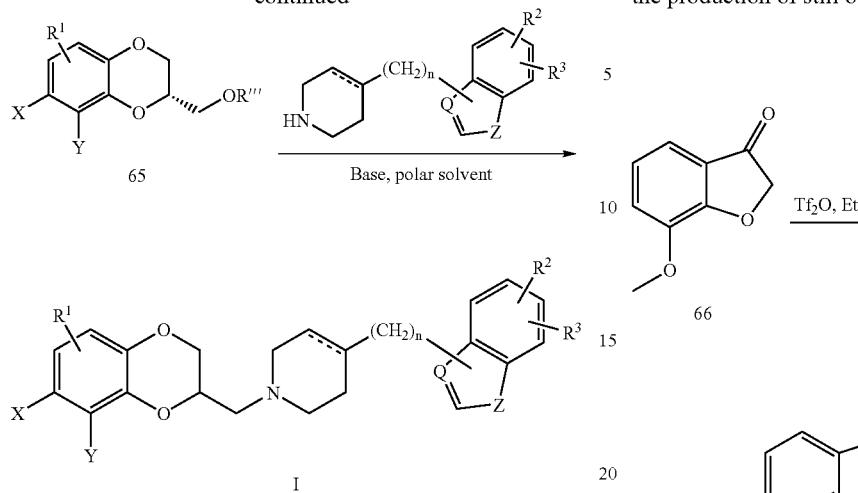

Deprotection of quinoline 63 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents such as hydrogen, cyclohexene, methyl cyclohexene, or ammonium formate gives the heterocycle-fused benzodioxanmethanol 64. The hydroxyl moiety of 64 can be activated with an aryl- or alkylsulfonyl chloride such as ptoluenesulfonyl chloride, methanesulfonyl chloride, 2-, 3- or 4-nitrobenzenesulfonyl chloride, or 2- or 4-bromobenzenesulfonyl chloride in the presence of bases such as triethylamine or pyridine in suitable solvents such as methylene chloride, THF, or toluene to afford 65 where R''' is a sulfonate such as ptoluenesulfonate, methanesulfonate, 2-, 3-, or 4-nitrobenzenesulfonate, or 2- or 4-bromobenzenesulfonate. The final coupling of 65 with piperidines appropriate to the invention, in the presence of bases such as Hünig's base (diisopropylethylamine), potassium carbonate, or sodium carbonate in polar solvents such as THF, dioxane, DMSO, DMF, or DMA affords the compounds of the invention I.

The phenols, guaiacols, catechols, 2',3',4'-trihydroxyacylphenones and benzodioxan methyltosylates appropriate to the above chemistry are known compounds or can be prepared by one schooled in the art. The appropriately substituted piperidines and tetrahydropyridines are known compounds or can readily be prepared by one schooled in the art, for example as illustrated in Scheme 18 below for 4-(7-methoxybenzofuran-3-yl)-1,2,3,6-tetrahydropyridine. The appropriately substituted benzofuranone (66) is converted to the triflate (67) by treatment with triflic anhydride and a tertiary base such as triethylamine. Conversion to the dioxaborolane (68) is effected by treatment with 4,4,5,5-tetramethyl-1,3,2-dioxaborolane in the presence of a tertiary base and a suitable palladium catalyst such as [1,1'-bis(diphenylphosphino)ferrocene]palladium (II) chloride. The dioxaborolane (68) is coupled with the appropriately protected azaheterocyclic triflate under Suzuki conditions involving a palladium catalyst such as tetrakis(triphenylphospine)palladium(0) to give (69), which following deprotection affords the substituted tetrahydropyridine (70) suitable for production of certain of the compounds of the invention. Reduction of the double bond in 70 by hydrogenation over a catalyst such as palladium on carbon gives the substituted piperidine, which is needed for the production of still other compounds of the invention.

Scheme 18

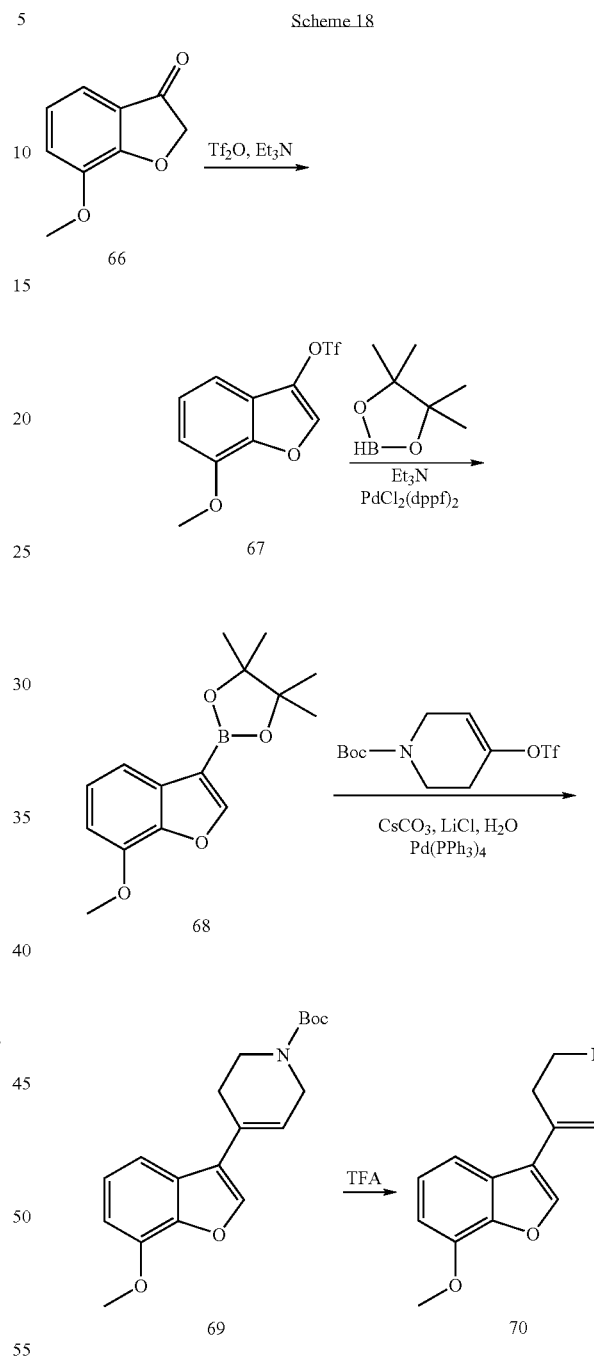

The substituted pyridines appropriate to Scheme 2 are known compounds or may be readily prepared by one schooled in the art by the method illustrated for 4-benzo[b]thiophen-7-yl-pyridine in Scheme 19 below. The suitably substituted bromobenzothiophene or bromobenzofuran (71) may be coupled with pyridine-4-boronic acid under Suzuki conditions involving a palladium catalyst such as [1,1'-bis(diphenylphosphino)ferrocene]palladium (II) chloride to give intermediates (72) useful for the production of the compounds of the invention.

Scheme 19

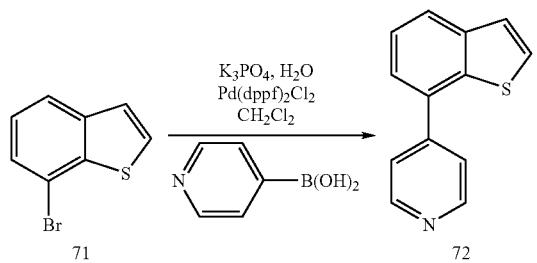

A protocol similar to that used by Cheetham et al. (*Neuropharmacol.* 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention arereported below as $K_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 9.25 | 4.89 | 498.5 (100) |
| Example 2 | 78.00 | 21.59 | |
| Example 3 | 18.50 | 15.88 | 436.6 (87.4) |
| Example 4 | 70.00 | 2.66 | 167.3 (91.0) |
| Example 5 | 35.00 | 23.43 | 1000.0 (30.0) |
| Example 6 | 8.50 | 14.53 | 145.5 (100) |
| Example 7 | 2.48 | 4.74 | 25.8 (100) |
| Example 8 | 33.00 | 3.45 | 146.9 (100) |
| Example 9 | 13.00 | 20.20 | 1978.0 (50.0) |
| Example 10 | 10.00 | 34.87 | 391.9 (40.5) |
| Example 11 | 213.00 | 15.71 | 15530.0 (70.0) |
| Example 12 | 109.00 | 8.67 | 589.6 (100) |
| Example 13 | 94.00 | 134.90 | 2516.0 (100) |
| Example 14 | 17.00 | 19.75 | 166.8 (100) |

Like the antidepressants fluoxetine, paroxetine and sertraline, the compounds of this invention have the ability to potently block the reuptake of the brain neurotransmitter secotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorders (including but not limited to trichotillomania), obsessive compulsive spectrum disorders (including but not limited to autism), social anxiety disorder, generalized anxiety disorder, obesity, eating disorders such as anorexia nervosa and bulimia nervosa, vasomotor flushing, cocaine and alcohol addiction, sexual dysfunction (including but not limited to premature ejaculation), incontinence (including, but not limited to fecal incontinence, urge incontinence, overflow incontinence, passive incontinence, reflex incontinence, stress urinary incontinence urinary exertional incontinence and urinary incontinence), and related illnesses. Moreover, the compounds of this invention have potent affinity for and antagonist activity at brain 5HT$_{1A}$ serotonin receptors. Recent clinical trials employing drug mixtures (eg, fluoxetine and pindolol) have demonstrated a more rapid onset of antidepressant efficacy for a treatment combining SSRI activity and 5HT$_{1A}$ antagonism (Blier and Bergeron, 1995; F. Artigas et al., 1996; M. B. Tome et al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remington's Pharmaceutical Sciences*, 17th edition, ed. Afonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutionsor suspensionss can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liqu ids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I, Ia and Ib. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Deliver Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

Intermediate 1

3-Allyloxy-4-methoxvnitrobenzene 97.5 g (0.51 mole) of the sodium salt of 5-nitroguaiacol was dissolved in one liter of DMF and 1.5 equivalentsof allyl bromide added. The reaction was heated to 65° C. for two hours, after which time much of the dark color had discharged and tic (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93-94° C.

Intermediate 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool, and poured into a mixture of 1 L ice and 1 L 2 N HCl. 73 Grams of crude but homogeneous (by tic 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61-62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

Intermediate 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70-75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$

Calc'd: C, 57.37; H, 5.21; N, 5.58

Found: C, 57.50; H, 5.21; N, 5.43

Intermediate 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid that formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$

Calc'd: C, 57.37; H, 5.21; N, 5.58

Found: C, 57.26; H, 5.20; N, 5.35

Intermediate 5

Toluene-4-sulfonic acid 8-allyl-7-nitro-2.3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60-62° C.) upon standing.

Elemental Analysis for: $C_{19}H_{19}NO_7S$

Calc'd: C, 56.29; H, 4.72; N, 3.45

Found: C, 56.13; H, 4.58; N, 3.44

Intermediate 6

{7-Nitro-8-[1-propenyl]-2.3-dihydro-1,4-benzo-dioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methyl-benzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105-106° C.) by evaporation of a pure E isomer-containing fraction.

Elemental Analysis for: $C_9H_{19}NO_7S$

Calc'd: C, 56.29; H, 4.72; N, 3.45

Found: C, 56.12; H, 4.64; N, 3.39

Intermediate 7

{7-Nitro-8-[3-oxo-1-propenyl]-2,3-dihydro-1,4-benzodioxin-2-yl}methyl 4-methylbenzenesulfonate {(2R)-7-nitro-8-[1-propenyl]-2,3-dihydro-1,4-benzo-dioxin-2-yl}methyl 4-methyl benzenesulfonate (6.15 g, 15.2 mmole) was dissolved in 180 mL of dioxane. Selenium dioxide (4.20 g, 37.9 mmole) was then added; followed by 0.70 mL of water. The heterogeneous mixture was heated at reflux under nitrogen for 5 hours. Upon cooling, the reaction was filtered and concentrated in vacuum to yield a dark yellow solid. This was dissolved in minimal: ethyl acetate and column chromatographed on silica gel using 30% ethyl acetate in hexane as eluant to give 5.75 g of the (R)-enantiomer of the title compound as a light yellow solid (m.p. 138-140° C.).

Elemental Analysis for: $C_{19}H_{17}NO_8S$

Calc'd: C, 54.41; H, 4.09; N, 3.34

Found: C, 54.10; H, 3.85; N, 3.31

Intermediate 8

2.3-Dihydro[1,4]dioxino[2.3-f]quinolin-2-ylmethyl 4-methylbenzenesulfonate

To a solution of {(2R)-7-nitro-8-[3-oxo-1-propenyl]-2,3-dihydro-1,4-benzodioxin-2-yl}methyl 4-methylbenzene-sulfonate (3.50 g, 8.35 mmole) in 200 mL of acetic acid/ethanol (1:1) was added 2.35 g (42.1 mmole) of iron powder and the mixture was heated at reflux under nitrogen for 8 hours. After the reaction was complete, 150 mL of water was added and the mixture filtered through a pad of celite. The filtrate was neutralized with saturated sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 1.85 g of the (R)-enantiomer of the title compound as a yellow oil.
$^1$H-NMR (CDCl$_3$): doublet 8.8 δ (1 H); doublet 8.2 δ (1 H); doublet 7.8 δ(2 H); doublet 7.6 δ (1 H); multiplet 7.35 δ (1 H); multiplet 7.25 δ (3 H); multiplet 4.6 δ (1 H); multiplet 4.3-4.4 δ (3 H); multiplet 4.2 δ (1 H); singlet 2.4 δ (3 H).

Intermediate 9

(8-Formyl-7-nitro-2,3-dihydro-1.4-benzodioxin-2-yl)methyl 4-methylbenzenesulfonate {(2R)-7-Nitro-8-[1-propenyl]-2,3-dihydro-1,4-beanzo-dioxin-2-yl}methyl 4-methyl benzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 minutes and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4-4.6 δ (2 H); multiplet 4.2 δ (3 H); singlet 2.4 δ (3 H).

Intermediate 10

{7-Nitro-8-[(E)-3-oxo-1-butenyl]-2,3-dihydro-1,4-benzodioxin-2-yl}methyl 4-methylbenzenesulfonate To a solution of 3.00 g (7.37 mmole) of [(2R)-8-formyl-7-nitro-2,3-dihydro-1,4-benzodioxin-2-yl]methyl 4-methylbenzenesulfonate in 250 mL of toluene was added 2.90 g (9.10 mmole) of 1-triphenylphosphorylidene-2-propanone. The mixture was stirred at room temperature under nitrogen for 5 hours, during which time some product precipitated from solution. The solvent was removed in vacuum and the crude residue was column chromatographed on silica gel with methylene chloride as eluant to give 3.0 g of the (R)-enantiomer of the title compound as a yellow solid. $^1$H-NMR (CDCl$_3$): doublet 7.8 δ (2 H); doublet 7.6 δ (1 H); doublet 7.5 δ (2 H); doublet 7.4 δ (2 H); doublet 6.95 δ (1 H); doublet 6.6 δ (1 H); multiplet 4.5 δ (1 H); doublet of doublets 4.0 δ (1 H); multiplet 4.2 δ (3 H); singlet 2.45 δ (3 H); singlet 2.4 δ (3 H).

Intermediate 11

(8-Methyl-2,3-dihydro[1,4]dioxino[2.3-f]quinolin-2-yl)methyl 4-methylbenzenesulfonate To a solution of {(2R)-7-nitro-8-[(E)-3-oxo-1-butenyl]-2,3-dihydro-1,4-benzodioxin-2-yl}methyl 4-methylbenzenesulfonate (3.40 g, 7.83 mmole) in 200 mL of acetic acid/ethanol (3:2) was added 2.25 g (40.2 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 2.5 g of the (R)-enantiomer of the title compound as a yellow oil. $^1$H-NMR (CDCl$_3$): doublet 8.1 δ (1 H); doublet 7.6 δ (2 H); doublet 7.45 δ (1 H); multiplet 7.2 δ (4 H); multipiet 4.6 δ (1 H); multiplet 4.3 δ (3 H); multiplet 4.1 δ (1 H); singlet 2.5 δ (3H); singlet 2.4 δ (3 H).

Intermediate 12

[7-Nitro-8-(2-oxoethyl)-2,3-dihydro-1,4-benzodioxin-2-yl]methyl 4-methylbenzenesulfonate A solution of 4.2 g (10 mmole) of toluene-4-sulfonic acid (2R)-8-allyl-7-nitro-2,3-dihydro-benzo(1,4)dioxin-2-ylmethyl ester in 400 mL of methylene chloride was cooled in a dry ice/isopropanol bath and saturated with ozone. It was then purged with oxygen and 2.6 g (20 mmole) of diisopropylethylamine added. The mixture was allowed to come to room temperature and stirred under nitrogen for 24 hours. It was then washed with 300 mL portions of 2 N HCl (aq), water and saturated brine, dried over magnesium sulfate, filtered and concentrated in vacuum to give 3.8 g of the (R)-enantiomer of the title compound as a white solid one-quarter hydrate, m.p. 116-120° C.

Elemental Analysis for: $C_{18}H_{17}NO_8S.0.25\ H_2O$

Calc'd: C, 52.49; H, 4.28; N, 3.40

Found: C, 52.33; H, 3.92; N, 3.36

Intermediate 13

2,3-Dihydro-7H-[1,4]dioxino[2,3-e]indol-2-ylmethyl 4-methylbenzenesulfonate

A mixture of 3.75 g (9.2mmole) of [(2R)-7-nitro-8-(2-oxoethyl)-2,3-dihydro-1,4-benzodioxin-2-yl]methyl 4-methylbenzenesulfonate and 3.0 g of platinum oxide in 50 mL of ethyl acetate was treated with 45 psi of hydrogen on a Parr hydrogenation apparatus for 6 hours. The mixture was then filtered through celite and concentrated in vacuum. The residue was column chromatographed on silica gel with first 10% hexane/methylene chloride, then 1% methanol/methylene chloride and finally 2% methanol/methylene chloride to give 1.50 g of the (R)-enantiomer of the title compound as a white solid one-quarter hydrate, m.p. 145° C.

Elemental Analysis for: $C_{18}H_{17}NO_5S.0.25\ H_2O$

Calc'd: C, 59.41; H, 4.85; N, 3.85

Found: C, 59.41; H, 4.57; N, 3.72

Intermediate 14

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmole) in DMF (75 mL) was added potassium carbonate (17.4 g, 126 mmole). After 5 minutes (R)-glycidyl tosylate (9.67 g, 42.3 mmole) was added, then the heterogeneous mixture was heated to 70° C. for 3 hours. After removal of the solvent in vacuum, the residue was taken into water (800 mL) and was then extracted with ethyl acetate (4×300 mL). The combined organic layers were dried over magnesium sulfate, filtered and evaporate to dryness in vacuum. The crude brown oil thus obtained was column chromatographed on silica gel with 40% hexane/ethyl acetate as eluant to give the (S)-enantiomer of the title compound as a yellow oil which solidifies upon standing (7.5 g, 78%). MS (ESI) m/z 223 (M–H)–.

Elemental Analysis for: $C_{11}H_{12}O_5.0.10\ H_2O$

Calc'd: C, 58.46; H, 5.44

Found: C, 58.02; H, 5.09

Intermediate 15

1-[5-Hydroxy-3-(hydroxymethyl)-2,3-dihydro-1,4-benzodioxin-6-yl]-1-ethanone oxime A solution of hydroxylamine hydrochloride (2.38 g, 34.2 mmole) in 1:1 ethanol/pyridine (100 mL) was added to a solution of 1-[(3S)-5-hydroxy-3-(hydroxymethyl)-2,3-dihydro-1,4-benzodioxin-6-yl]-1-ethanone (1.92 g, 8.57 mmole) in ethanol (200 mL). It was then heated to reflux under nitrogen for 5 hours. Upon cooling, the solvent was removed and replaced with ethyl acetate. The solution was then washed with water (200 mL) and with aqueous 2N HCl (100 mL), dried over magnesium sulfate, filtered and evaporated in vacuum to give 1.89 g (93%) of the (S)-enantiomer of the title compound as a gray solid, m.p. 162° C. MS (ESI) m/z 240 (M+H)+.

Elemental Analysis for: $C_{11}H_{13}NO_5.0.35\ H_2O$

Calc'd: C, 53.81; H, 5.62; N, 5.71

Found: C, 53.51; H, 5.30; N, 5.58

Intermediate 16

[2-Methyl-7,8-dihydro[1,4]dioxino[2,3-g][1,3]benzoxazol-8-yl]methanol 3.03 g (12.6 mmole) of 1-[(3S)-5-hydroxy-3-(hydroxymethyl)-2,3-dihydro-1,4-benzodioxin-6-yl]-1-ethanone oxime was dissolved in a mixture of 1:3 N,N-dimethylacetamide/acetonitrile (100 mL). The solution was cooled in an ice/water bath and a solution of phosphorus oxychloride (1.26 mL, 35 mmole) in 1:3 N,N-dimethylacetamide/acetonitrile (30 mL) was added. The reaction mixture was stirred under nitrogen over a period of 48 hours. It was then added to an ice cold, saturated solution of sodium acetate, extracted with ethyl acetate, dried over magnesium sulfate, filtered and evaporated in vacuum. The resulting crude oil was column chromatographed on silica gel with 60% hexane/ethyl acetate to remove impurities and the product eluted with 40% hexane/ethyl acetate. After evaporation of the solvent in vacuum, 2.08 g (75%) of the (S)-enantiomer of the title compound was obtained as a white solid, m.p. 120° C. MS (ESI) m/z 222 (M+H)+.

Elemental Analysis for: $C_{11}H_{11}NO_4.0.20\ H_2O$

Calc'd: C, 58.77; H, 5.11; N, 6.23

Found: C, 58.93; H, 4.91; N, 6.14

Intermediate 17

[2-Methyl-7,8-dihydro[1,4]dioxino[2,3-g][1,3]benzoxazol-8-yl]methyl 4-methylbenzenesulfonate To a solution of [(8S)-2-methyl-7,8-dihydro[1,4]dioxino[2,3-g][1,3]benzoxazol-8-yl]methanol (1.80 g, 8.14 mmole) in methylene chloride (100 mL) was added p-toluenesulfonyl chloride (3.90 g, 20.4 mmole). The mixture was cooled in an ice bath and a solution of diisopropylethylamine (3.55 mL, 20.4 mmole) in methylene chloride (20 mL) was then added dropwise, followed by 4-dimethylaminopyridine (0.65 g, 5.30 mmole). The solution was allowed to warm to room temperature and was stirred under nitrogen overnight. The reaction was diluted to 500 mL in volume with methylene chloride, then washed with aqueous 2 N HCl (200 mL), with saturated aqueous sodium bicarbonate (200 mL), and with brine (150 mL), dried over magnesium sulfate, filtered and evaporated in vacuum to a yellow oil. The crude oil was column chromatographed on silica gel using methylene chloride to remove impurities and 3% methanol/methylene chloride to elute the (R)-enantiomer of the title compound, which becomes a white solid under vacuum (2.56 g, 84%), m.p. 123° C. MS (ESI) m/z 376 (M+H)+.

Elemental Analysis for: $C_{18}H_{17}NO_6S.0.20\ H_2O$

Calc'd: C, 57.04; H, 4.63; N, 3.70

Found: C, 56.75; H, 4.62; N, 3.51

Intermediate 18

5-Bromo-6-methoxy-2-methylquinoline

A solution of 6-methoxy-2-methylquinoline (177 g, 1.02 mol) in acetonitrile (1.77 L) was cooled to 0-3° C. followed by portion-wise addition of N-bromo-succinimide (200 g, 1.12 mol) over a period of 30 min while maintaining the same temperature. The resulted brown slurry was warmed to ambient temperature and stirred for an additional 6 h. The reaction was then quenched by a 10% $NaHSO_3$ solution (211 mL). The reaction mixture was concentrated to a volume of 600 mL then slowly poured into 0.1 N NaOH (2.5 L). The slurry (pH=9) was stirred at room temperaturefor 1 h then filtered, washed with water (2×1 L) and dried in a vacuum oven to give 253 g (98.6%) of the title compound as a brown solid. $R_f$=0.39 (3:7) EtOAc:heptane; $^1H$ NMR (DMSO) δ 8.30 (d, J=6.5 Hz, 1H), 7.98 (d, J=6.9 Hz, 1H), 7.70 (d, J=7.0 Hz,1 H), 7.47 (d, J=6.5 Hz, 1H), 4.02 (s, 3H), 2.66 (s, 3H);

Elemental Analysis for: $C_{11}H_{10}NOBr$

Calc'd: C 52.40 H 3.97 N 5.56

Found: C 52.13 H 3.94 N 5.61

Intermediate 19

5-Bromo-2-methyl-6-quinolinol

A mixture of 5-bromo-2-methyl-6-methoxyquinoline (30 g, 0.12 mol) in 48% HBr (135 mL) was heated to reflux for 7 h then cooled to 5° C. in 1 h to give a brown and thick slurry. The slurry was stirred at 0-5° C. for 1 h then filtered, washed with EtOAc (2×50 mL) and dried in a vacuum oven to give 34.9 g (92%) of the hydrobromide of the title compound as a brown solid. $^1H$ NMR (DMSO) δ 8.26 (d, J=8.7 Hz, 1H), 7.85 (d, J=9.1 Hz, 1H), 7.56 (d, J=9.1 Hz, 1H), 7.45 (d, J=8.7 Hz, 1H), 2.64 (s, 3H). A slurry of the hydrobromide salt of 5-bromo-2-methyl-6-quinolinol (3.4 g, 10.5 mmol) and Amberlyst A-21 ion-exchange resin (1.7 g, pre-washed with MeOH then dried in oven) in MeOH (35 mL) was stirred at room temperature for 3 h. The mixture was then filtered and concentrated in vacuo to give 2.5 g (100%) of a yellow solid. $R_f$=0.36 (1:1) EtOAc:heptane; $^1H$ NMR (DMSO) δ 8.26 (d, J=8.4 Hz, 1H), 7.82 (d, J=9.3 Hz, 1H), 7.47 (t, J=9.1 Hz, 2H), 2.66 (s, 3H).

Intermediate 20

(2S)-1-(Benzyloxy)-3-[(5-bromo-2-methyl-6-quinolinyl)oxy]-2-propanol

A solution of 5-bromo-2-methyl-6-quinolinol (30.1 9, 126 mmol), (R)-benzyl glycidyl ether (24.9 g, 152 mmol) and triethylamine (17.4 g, 172 mmol) in DMA (200 mL) was heated in a 95-98° C. oil bath for 2 days. The solution was cooled and poured into water (300 mL) while stirring. The tan precipitate formed was filtered, washedwith water (100 mL) and dried in a vacuum oven to give 37 g (73%) of the title compound as a tan solid. $R_f$=0.35 (EtOAc); $^1H$ NMR (DMSO) δ 8.31 (d, J=8.8 Hz,1H), 7.96 (d, J=9.2Hz,1H), 7.72(d, J=9.3 Hz, 1H), 7.74 (d, J=8.7Hz, 1H), 7.25-7.36 (m, 5H), 5.28 (d, J=5.1 Hz, 1H), 4.56 (s, 2H), 4.22-4.29 (m, 2H), 4.08-4.15 (m, 1H), 3.61-3.73 (m, 2H), 2.66 (s, 3H); Specific rotation=+6.2° (c=1, $CH_3OH$);

Elemental Analysis for: $C_{20}H_{20}BrNO_3$

Calc'd: C 59.66 H 4.97 N 3.48

Found: C 59.43 H 4.97 N 3.55

Intermediate 21

(2S)-2[(Benzyloxy)methyl-8-methyl-2.3-dihydro[1,4]dioxino [2,3-f]quinoline

To a mixture of (2S)-1-(benzyloxy)-3-[5-bromo-2-methyl-6-quinolinyl)oxyl]-2- propanol (100 g, 0.249 mol) and copper (I) iodide (47.4 g, 0.249 mol) in toluene (2 L), NaH (10.9 g, 0.45 mol) was added in portions at 30-35° C. over 20 min. The reaction mixture was kept at 35° C. for 30 minutes then heated to 110° C. slowly. After 30 minutes, the reaction was cooled to 60° C., additional NaH (10.9 g, 0.45 mol) was added. This was warmed to 110° C. for an additional 2 hours then cooled to rt before dropwise addition of water (200 mL). After stirring for 15 minutes, the mixture was filtered through a bed of celite then washed with toluene (3×50 mL) and water (50 mL). The two layers were separated. The organic layer was extracted with water (100 mL), $NH_4OH$ (100 mL), 25% NaCl (100 mL) and concentrated in vacuo to give 387.6 g of the crude product as a brown syrup. The crude product was carried through to the debenzylation step before purification.

Intermediate 22

[(2R)-8-Methyl-2.3-dihydro[1,4]dioxino[2,3-f] quinolin-2-yl]methanol

To a solution of (2S)-2[(benzyloxy)methyl-8-methyl-2,3-dihydro[1,4]dioxino [2,3-f]quinoline (0.16 g, 0.5 mmol) in EtOH (1 mL) was added cyclohexene (0.5 mL) then 10% Pd/C (0.016 g, 10 mol %). The mixture was heated to reflux under $N_2$ for 18 h then cooled and filtered. The catalyst was rinsed with methanol and the filtrate was concentrated in vacuo to afford 0.113 g (98%) of the title alcohol as an off-white solid.
$^1$H NMR ($CD_3OD$) δ 8.46 (m, 1H), 7.47 (m, 1H), 7.38-7.31 (m, 2H), 4.40 (m, 1H), 4.36 (m, 1H), 4.18 (m, 1H), 3.91 (m, 2H), 2.68 (s, 3H).

Intermediate 23

[(2R)-8-Methyl-2,3-Dihydro[1,4]Dioxino[2,3-f] Quinolin-2-yl]Methyl 4-Bromobenzenesulfonate A solution of [(2S)-8-methyl-2,3-dihydro[1,4]dioxino[2,3-f]quinolin-2-yl]-methanol (4.0 g, 17.3 mmol), brosyl chloride (4.86 g, 19.0 mmol), dimethylamino pyridine (20 mg, 0.16 mmol) and triethylamine (3.62 mL, 25.8 mmol) in toluene (40 mL) was stirred at 60° C. for 6 h. The reaction mixture was cooled to room temperature then water (20 mL) was added. After 30 min, the two layers were separated. The organic layer was extracted with 8% $NaHCO_3$ (20 mL) and $H_2O$ (20 mL), dried over $Na_2SO_4$, filtered and concentrated in vacuo. The solid obtained was dissolved in isopropyl alcohol (50 mL) and toluene (10 mL) at 80° C., cooled to room temperature over 1 h then filtered, washed with (5:1) IPA: toluene (2×5 mL) and dried in a vacuum oven to give 5.99 g (76.9%) of the title compound as an off-white solid. $^{13}$C NMR ($CDCl_3$) δ 157.9, 144.3, 138.1, 134.7, 132.9, 129.7, 129.6, 129.0, 122.4, 121.7, 121.3, 118.8, 70.7, 67.6, 64.5, 25.4

EXAMPLE 1

2-(4-Benzo[b]thiophen-3-yl-3,6-dihydro-2H-pyridin-1-ylmethyl)-8-methyl-2,3-dihydro-[1,4]dioxino[2,3-f]quinoline To a mixture of [(2R)-8-methyl-2,3-dihydro[1,4]dioxino [2,3-f]quinolin-2-yl]methyl 4-toluenesulfonate (0.87 g, 2.3 mmol) and 4-benzo[b]thiophen-3-yl-1,2,3,6-tetrahydro-pyridine (0.48 g, 2.2 mmol) was added 3 mL of dimethylsulfoxide. The mixture was stirred at 97° C. for 18 hours. The solvent was evaporated under reduced pressure. The residue was partitioned between 500 mL each of methylene chloride and saturated aqueous sodium bicarbonate. The methylene chloride layer was washed once with 500 mL of water and dried over anhydrous magnesium sulfate. Filtration and concentration in vacuum gave 0.91 g of oil. This was chromatographed on silica gel with a gradient, of ethyl acetate and hexane. The product fractions were collected to give 0.059 g of the free base as pure, yellow oil. This was dissolved in ethanol and heated. Oxalic acid dihydrate (0.0125 g, 0.0991 mmol) in ethanol was added. After the mixture had cooled, filtration gave 0.0619 g of the S enantiomer of the title compound as an orange oxalate salt, m.p. 129-133° C.

Elemental Analysis for: $C_{26}H_{24}N_2O_2S.C_2H_2O_4.\frac{2}{3} H_2O$

Calc'd: C, 63.38; H, 5.19; N, 5.28

Found: C, 63.48; H, 4.97; N, 5.08

EXAMPLE 2

2-(4-Benzo[b]thiophen-2-yl-3,6-dihydro-2H-pyridin-1-ylmethyl)-8-methyl-2,3-dihydro-[1,4]dioxino[2,3-f]quinoline To a mixture of [(2R)-8-methyl-2,3-dihydro[1,4]dioxino [2,3-f]quinolin-2-yl]methyl 4-toluenesulfonate (0.638 g, 1.66 mmol) and 4-benzo[b]thiophen-2-yl-1,2,3,6-tetrahydro-pyridine (0.46 g, 2.1 mmol) was added 12 mL of dimethylsulfoxide. The mixture was stirred at 90° C. for 18 hours. The solvent was evaporated under reduced pressure. The residue was partitioned between 500 mL each of methylene chloride and saturated aqueous sodium bicarbonate. The methylene chloride layer was washed with water twice and dried over anhydrous magnesium sulfate. Evaporation of the solvent gave 0.98 g of oil. This was chromatographed on silica gel with a gradient of ethyl acetate and hexane. The product fractions were collected and concentrated in vacuum to give 0.39 g of the title compound as nearly pure, light yellow oil. This was triturated with ethanol to give 0.2563 g of the S enantiomer of the title compound as a light yellow solid, m.p. 174-176° C.

Elemental Analysis for: $C_{26}H_{24}N_2O_2S. \frac{1}{4} H_2O$

Calc'd: C, 72.11; H, 5.70; N, 6.47

Found: C, 72.01; H, 5.42; N, 6.32

EXAMPLE 3

2-[4-(5-Fluoro-benzo[b]thiophen-3-yl)-3,6-dihydro-2H-pyridin-1-ylmethyl]-8-methyl-2,3-dihydro-[1,4]dioxino[2,3-f]quinoline To a solution of [(2R)-8-methyl-2,3-dihydro[1,4]dioxino[2,3-f]quinolin-2-yl]methyl 4-toluenesulfonate (0.50 g, 1.1 mmol), 4-(5-fluoro-benzo[b]thiophen-3-yl)-1,2,3,6-tetrahydropyridine (0.35 g, 1.5 mmol), 21 mL of THF and 21 mL of DMF was added NaHCO3 (0.45 g, 5.4 mmol. The mixture was stirred at reflux for 18 hours. The solvent was removed in vacuum and the residue partitioned between 500 mL each of methylene chloride and water. The methylene chloride layer was washed with water 3 times and dried over anhydrous magnesium sulfate. Filtration and concentration in vacuum gave 0.62 g of dark oil. This was chromatographed on silica gel with a gradient of ethyl acetate and hexane to give 0.12 g of the free base as a pure light yellow oil. The oil was dissolved in ethanol and added to a solution of oxalic acid dihydrate (0.0400 g, 0.317 mmol) in ethanol. Filtration gave 0.0871 g of the S enantiomer of the title compound as a yellow oxalate, m.p. 197-201° C.

Elemental Analysis for: $C_{26}H_{23}FN_2O_2S.C_2H_2O_4.2\ H_2O$

Calc'd: C, 58.73; H, 5.10; N, 4.89

Found: C, 58.78; H, 4.46; N, 4.63

Intermediate 24

Trifluoro-methanesulfonic acid 7-methoxy-benzofuran-3-yl ester

To a cold solution (−20° C.) of 3.3 g (20 mmol) 7-methoxy-benzofuranone in 30 mL methylene chloride was added 8.3 mL (6.0 mmol) of triethylamine. To the cold mixture, a solution of 8.5 g (30 mmol) of triflic anhydride in 20 ml of methylene chloride was added dropwise. The temperature was kept at −20° C. or 1 hour. The reaction was then quenched with 100 mL of saturated aqueous sodium bicarbonate aand extracted with methylene chloride (2×150 mL). The combined organic extracts were dried over magnesium sulfate and concentrated in vacuum to give 5.6 g of the desired product. MS (ES) m/z (relative intensity): 265 (M+H,100);

Intermediate 25

2-(7-Methoxvbenzofblfuran-3-yl0-4,4,5,5-tetramethyl-[1,2]oxaborolane

To a mixture of trifluoro-methanesulfonic acid 7-methoxy-benzofuran-3-yl ester (0.660 g, 2.23 mmol)) in triethylamine (1 ml) was added first 3.75 mL (3.75 mmol) of 1 N pinacoleborane in THF followed by 0.10 g of [1,1'-bis(diphenylphosphino)ferrocene]palladium (II) chloride/methylene chloride 1:1 complex. The reaction was heated at 150° C. for 3 minutes in the microwave. The solvent was removed under vacuum. The residue was taken up in 300 mL of water and extracted with ether (2×200 mL). The combined organic extracts were dried over magnesium sulfate, filtered and the solvent removed in vacuum. The residue was filtered through 50 mL of silica gel using 10% ethyl acetate/hexane to give 0.350 g of the title compound. 1H NMR (300 MHz, CDCl$_3$); δ 1.36 (s, 12H), 4.01 (s, 3H), 6.81 (d, 1H), 7.18 (t, 1H), 7.52 (d, 1H), 7.95 (s, 1H).

Intermediate 26

4-(7-Methoxy-benzofuran-3-yl)-3,6-dihydro-2H-pyridine-1-carboxylic acid tert-butyl ester To a solution of 2-(7-methoxybenzo[b]furan-3-yl)-4,4,5,5-tetramethyl-[1,2]oxaborolane (1.10 g, 4.0 mmol) in dimethoxyethane (1 mL) was added CsCO$_3$ (0.650 g, 2.0 mmol), H$_2$O (1 mL), 4-trifluoromethanesulfonyloxy-3,6-dihydro-2H-pyridine-1-carboxylic acid tert-butyl ester (0.480 g, 1.45 mmol), LiCl (0.10 g, 2.4 mmol) and tetrakis(triphenylphosphine)palladium (0) (0.06 g, 0.05 mmol). The reaction was heated in the microwave for 5 min at 150° C. The solvent was removed in vacuum, the residue taken up in 300 mL of methylene chloride, washed with 200 mL portions of saturated aqueous sodium carbonate and 1 N NH$_4$OH (aq), dried over anhydrous sodium sulfate, filtered and concentrated in vacuum. The residue was filtered through 150 mL of silica gel with 15% ethyl acetate/hexane as eluant to give 0.50 g of the title compound. 1 H NMR (300 MHz, CDCl$_3$); δ 1.5 (s, 9H), 2.51 (t, 2H), 3.66 (t, 2H), 4.04 (s, 3H), 4.12 (dd,2H), 6.24 (brs, 1H), 6.91 (d, 1H), 7.17 (t, 1H), 7.39 (d, 1H), 7.59 (s, 1H), MS (ES) m/z (relative intensity): 330 (M+H,100).

Intermediate 27

4-(7-Methoxy-benzofuran-3-yl)-1,2,3,6-tetrahydropyridine

To a solution of 4-(7-methoxy-benzofuran-3-yl)-3,6-dihydro-2H-pyridine-1-carboxylic acid tert-butyl ester (0.50 g, 1.5 mmol) in methylene chloride (10 mL), was added drop wise a solution of TFA (1 mL) in methylene chloride (5mL). The reaction was stirred at room temperature for one hour, then was diluted with 250 mL of methylene chloride, washed with 1N NaOH (100 mL) and with saturated brine, dried over magnesium sulfate, filtered and concentrated in vacuum to give 0.30 g of the title compound. 1H NMR (300 MHz, CDCl$_3$); δ 2.5 (t, 2H), 3.19 (t, 2H), 3.64 (dd,2H), 4.01 (s, 3H), 6.30 (br s, 1H), 7.10 (d, 1H), 7.21 (t, 1H), 7.52 (d, 1H), 7.64 (s, 1H); MS (ES) m/z (relative intensity): 230 (M+H,100).

EXAMPLE 4

2-[4-(7-Methoxy-benzofuran-3-yl)-3,6-dihydro-2H-pyridin-1-ylmethyl]-8-methyl-2,3-dihydro-[1,4]dioxino[2,3-f]guinoline A mixture of [(2R)-8-methyl-2,3-dihydro[1,4]dioxino[2,3-f]quinolin-2-yl]methyl 4-bromobenzenesulfonate ester (0.173 g, 0.38 mmol), 4-(7-methoxybenzofuran-3-yl)-1,2,3,6-tetrahydropyridne (0.10 g, 0.44 mmol) and potassium carbonate (0.145 g, 1.0 mmol) in 2 mL of N,N-dimethylformamide was stirred under nitrogen at room temperature for 2 days and then at 60° C. for 6 hours. Water was added and the resulting precipitate was filtered, dried and column chromatographed on 100 mL of silica gel using first 50% ethyl acetate in hexane and then 75% ethyl acetate/hexane as eluant. Combination and concentration of the product fractions gave 0.015 g of the S enantiomer of the title compound as a yellow solid. MS (ESI) m/z 443 (M+H)+.

EXAMPLE 5

2-[4-(5-Fluoro-benzo[b]thiophen-3-yl)-3,6-dihydro-2H-pyridin-1-ylmethyl]-2,3-dihydro-[1,4]dioxino[2,3-f]quinoline To a solution [(2R)-8-methyl-2,3-dihydro[1,4]dioxino[2,3-f]quinolin-2-yl]methyl 4-toluenesulfonate (0.51 g, 1.4 mmol), 4-(5-fluoro-benzo[b]thiophen-3-yl)-1,2,3,6-tetrahydro-pyridine (0.39 g, 1.7 mmol), 24 mL of THF and 24 mL of DMF was added $NaHCO_3$ (0.50 g, 5.9 mmol). The mixture was stirred and heated at reflux for 18 hours. The solvents were evaporated in vacuum and the residue was partitioned between 500 mL portions of ethyl acetate and water. The ethyl acetate layer was washed with water and dried over anhydrous magnesium sulfate. Filtration and concentration in vacuum gave 0.731 g of oil. This was chromatographed on silica gel with a gradient of ethyl acetate and hexane. Only the fractions clean enough to use were combined. They were concentrated to give 0.13 g of the free base as an oil. This was dissolved in ethanol. A solution of oxalic acid dihydrate (0.0410 g, 0.325 mmol) in ethanol was added. Filtration gave 0.11 g of the S enantiomer of the title compound as a light yellow oxalate, m.p. 183–185° C.

Elemental Analysis for: $C_{25}H_{21}FN_2O_2S.C_2H_2O_4.H_2O$

Calc'd: C, 59.99; H, 4.66; N, 5.18

Found: C, 60.05; H, 4.39; N, 4.97

EXAMPLE 6

2-(4-Benzo[b]thiophen-3-yl-3,6-dihydro-2H-pyridin-1-ylmethyl)-2,3-dihydro-[1,4]dioxino[2,3-f]quinoline To a solution of [(2R)-2,3-dihydro[1,4]dioxino[2,3-f]quinolin-2-yl]methyl toluenesulfonate (0.43 g, 1.2 mmol), 4-benzo[b]thiophen-3-yl-1,2,3,6-tetrahydro-pyridine (0.31 g, 1.4 mmol), 21 mL of THF and 21 mL of DMF was added $NaHCO_3$ (0.43 g, 5.1 mmol). The mixture was stirred and heated at 60° C. for 2 days and then allowed to stand at room temperature for one day. The solvent was evaporated in vacuum. The residue was partitioned between 500 mL each of ethyl acetate and water. The ethyl acetate layer was washed with water four times and then dried over anhydrous magnesium sulfate. Filtration and concentration in vacuum gave 0.24 g of oil. This was chromatographed on silica gel with a gradient of ethyl-acetate- and hexane to give 0.06 g of the free base as an oil. This was dissolved in ethanol and added to a solution of oxalic acid dihydrate (0.021 g, 0.17 mmol) in ethanol. Filtration gave 0.042 g of the S-enantiomer of the title compound as a yellow oxalate, m.p. 178–180° C.

Elemental Analysis for: $C_{25}H_{22}N_2O_2S.C_2H_2O_4.1.6 H_2O$

Calc'd: C, 60.80; H, 5.14; N, 5.25

Found: C, 60.59; H, 4.79; N, 5.00

EXAMPLE 7

2-(4-Benzo[b]thiophen-3-yl-3,6-dihydro-2H-pyridin-1-ylmethyl)-2,3-dihydro-7H-[1,4]dioxino[2,3-e]indole To a solution of [(2R)-7,8-dihydro-3H-6,9-dioxa-3-aza-cyclopenta[a]naphthalen-8-yl]methyl toluene-4-sulfonate (0.6 g, 2 mmol), ), 4-benzo[b]thiophen-3-yl-1,2,3,6-tetrahydro-pyridine ( 0.04 g, 0.2 mmol), 30 mL of THF and 25 mL of DMF was added $NaHCO_3$ (0.6 g, 7 mmol). The mixture was stirred and heated at 70° C. for 1 day and then allowed to stand at room temperature for 3 days. The solvent was evaporated in vacuum. The residue was partitioned between 500 mL each of ethyl acetate and water. The ethyl acetate layer was washed with water four times and dried over anhydrous magnesium sulfate. Filtration and concentration in vacuum gave 0.86 g of oil. This was chromatographed on silica gel with a gradient of ethyl acetate and hexane to give 0.25 g of the free base as a very light tan oil. This was dissolved in ethanol. A solution of oxalic acid dihydrate (0.0851 g, 0.675 mmol) in ethanol was added. Filtration gave 0.1436 g of the S enantiomer of the title compound as a light cream color amorphous oxalate.

Elemental Analysis for: $C_{24}H_{22}N_2O_2S.C_2H_2O_4$

Calc'd: C, 63.36; H, 4.91; N, 5.68

Found: C, 63.22; H, 4.86; N, 5.50

EXAMPLE 8

2-[4-(5-Fluoro-benzo[b]thiophen-3-yl)-3,6-dihydro-2H-pyridin-1-ylmethyl]-2,3-m-dihydro-7H-[1,4]dioxino[2,3-e]indole To a mixture of [(2R)-7,8-dihydro-3H-6,9-dioxa-3-aza-cyclopenta[a]naphthalen-8-yl]methyl 4-toluenesulfonate (0.67 g, 1.9 mmol), 4-(5-fluoro-benzo[b]thiophen-3-yl)-1,2,3,6-tetrahydro-pyridine (0.48 g, 2.1 mmol) and $Na_2CO_3$ (0.80 g, 7.5 mmol) was added 21 mL of dimethylsulfoxide. The mixture was stirred heated at 70° C. for 18 hours. TLC on silica gel showed much tosylate was unreacted. Stirring and heating at 80° C. was continued for 18 hours. The solvent was evaporated at reduced pressure. The residue was partitioned between 500 mL portions of ethyl acetate and water. The ethyl acetate layer was washed five times with water and dried over anhydrous magnesium sulfate. Filtration and concentration in vacuum gave 0.86 g of dark oil. This was chromatographed on silica gel with 40% ethyl acetate in hexane to give 0.29 g of the free base as a light tan oil. This was dissolved in ethanol and added to a solution of oxalic acid dihydrate (0.0978 g, 0.776). Filtration gave 0.1049 g of the S enantiomer of the title compound as a light gray amorphous oxalate.

Elemental Analysis for: $C_{24}H_{21}FN_2O_2S.C_2H_2O_4.0.2 H_2O$

Calc'd: C, 60.74; H, 4.59; N, 5.45

Found: C, 60.72; H, 4.34; N, 5.26

EXAMPLE 9

8-(4-Benzo[b]thiophen-3-yl-3,6-dihydro-2H-pyridin-1-ylmethyl)-2-methyl-7,8-dihydro-[1,4]dioxino[2,3-g][1,3]benzoxazole To a mixture of [(2R)-2-methyl-7,8-dihydro-1,6,9-trioxa-3-aza-cyclopenta[a]naphthalen-8-yl]methyl 4-toluenesulfonate (0.3081 g, 0.8207 mmol) and 4-benzo[b]thiophen-3-yl-1,2,3,6-tetrahydro-pyridine (0.54 g, 2.5 mmol) was added 10 mL of dimethylsulfoxide. The solution was stirred and heated at 85° C. for 4.5 hours. The solvent was evaporated under reduced pressure. The residue was partitioned between 500 mL each of ethyl acetate and saturated aqueous sodium bicarbonate. The ethyl acetate layer was washed four times with water. Drying over magnesium sulfate, filtration and evaporation of the solvent gave 0.55 g of oil. This was eluted from silica gel with a gradient of hexane and ethyl acetate to give 0.09 g of the free base as an oil. This was dissolved in EtOH and added to a solution of oxalic acid dihydrate 0.0304 g, 0.241 mmol) in ethanol. Filtration gave 0.0948 g of the S enantiomer of the title compound as a fine white oxalate, m.p. 126-129° C.

Elemental Analysis for: $C_{24}H_{22}N_2O_3S.C_2H_2O_4.0.5\ H_2O$

Calc'd: C, 60.34; H, 4.87; N, 5.41

Found: C, 60.36; H, 4.99; N, 5.26

Intermediate 28

4-Benzo[b]thiophen-7-yl-pyridine

To 7-bromo--benzo[b]thiophene (5.28 g, 24.7 mmol) was added pyridine-4-boronic acid (2.734 g, 22.24 mmol), $K_3PO_4$ (12.0 g, 56.5 mmol), 37.5 mL of 1,4-dioxane and 3.8 mL of water. The mixture was placed under vacuum for several minutes and flushed with nitrogen. This was repeated 5 times. $Pd(dppf)Cl_2.CH_2Cl_2$ (0.909 g, 1.11 mmol), $PdCl_2$ (0.1994 g, 1.124 mmol) and 1,1"-bis(diphenylphosphino)ferrocene (0.6234 g, 1.124 mmol) were purged in the same way using high vacuum. The catalyst was added to the reaction flask, which was purged again 3 times. The mixture was stirred at 80° C. under nitrogen. After 1 day TLC showed much starting material remained. Additional $K_3PO_4$ (2.3 g, 10.8 mmol) was added after purging. Stirring at 80° C. under nitrogen was continued for 12 to 14 hours and then at room temperature till the next day. The mixture was partitioned between water and ethyl acetate, filtered through Celite and the layers separated. The organic layer was concentrated in vacuum. The residue was redissolved in ethyl acetate, washed with water and dried over magnesium sulfate. Concentration in vacuum gave 6.06 g of dark oil. This was eluted from silica gel with a gradient of hexane and ethyl acetate to give 2.43 g of the title compound as a tan oil that crystallizes slowly, (m.p.71-72° C.).

Elemental Analysis for: $C_{13}H_9NS.⅓\ H_2O$

Calc'd: C, 71.86; H, 4.48; N, 6.45

Found: C, 71.93; H, 4.37; N, 5.66

Intermediate 25

S-4-Benzo[b]thiophen-7-yl-1-(8-methyl-2,3-dihydro-[1,4]dioxino[2,3-f]quinolin-2-ylmethyl)-pyridinium 4-bromo-benzenesulfonate To a mixture of [(2R)-8-methyl-2,3-dihydro[1,4]dioxino [2,3-f]quinolin-2-yl]methyl 4-bromobenzenesulfonate (1.00 g, 2.22 mmol) and 4-benzo[b]thiophen-7-yl-pyridine (0.58 g, 2.7 mmol) was added 4 mL of benzene. The mixture was stirred at 75° C. for 18 hours, after which time most of the solvent had evaporated. TLC on silica gel showed much of the starting material remained. The reaction mixture stood at room temperature and open to the atmosphere for several days. The residual tar was triturated with acetone at 52° C. to give a solid. The solid was broken up and the volume was reduced by evaporation to approximately 20 mL. Filtration gave 0.6581 g of the title compound as a gray solid, (dec.>175° C.).

Elemental Analysis for: $C_{32}H_{25}BrN_2O_5S_2.2\ H_2O$

Calc'd: C, 55.09; H, 3.61; N, 4.02

Found: C, 55.13; H, 3.88; N, 3.77

EXAMPLE 10

2-(4-Benzo[b]thiophen-7-yl-3,6-dihydro-2H-pyridin-1-ylmethyl)-8-methyl-2,3-dihydro-[1,4]dioxino[2,3-f]quinoline To a stirring suspension of S-4-benzo[b]thiophen-7-yl-1-(8-methyl-2,3-dihydro-[1,4]dioxino[2,3-f]quinolin-2-ylmethyl)-pyridinium 4-bromo-benzenesulfonate ((0.5060 g, 0.7648 mmol) in 4.5 mL of EtOH cooled in an ice-bath was added sodium borohydride (0.045 g, 1.2 mmol). This was stirred until it had warmed almost to room temperature. TLC on silica gel showed product and maybe some starting material. A slight excess of sodium borohydride was added to the mixture stirring at 0° C. The reaction was allowed to stir and warm to room temperature overnight. The solvent wasevaporated at reduced. pressure. The residue was partitioned between ethyl acetate and water. The ethyl acetate layer was washed with water twice and dried over anhydrous magnesium sulfate. Filtration and concentration in vacuum gave 0.31 g of oil. This was chromatographed on silica gel with a gradient of ethyl acetate and hexane to give 0.1307 g of the free base as an oil. This was dissolved in EtOH and added to a solution of oxalic acid dihydrate (0.0426 g, 0.338 mmol) in ethanol. Filtration gave 0.1237 g of the S enantiomer of the title compound as a white solid oxalate, m.p. 183-185° C.

Elemental Analysis for: $C_{26}H_{24}N_2O_2S.C_2H_2O_4.⅓\ H_2O$

Calc'd: C, 64.11; H, 5.12; N, 5.34

Found: C, 64.01; H, 5.05; N, 5.28

EXAMPLE 11

2-(4-Benzofuran-2-yl-3,6-dihydro-2H-pyridin-1-ylmethyl)-8-methyl-2,3-dihydro-[1,4]dioxino[2,3-f]quinoline A mixture of [(2R)-8-methyl-2,3-dihydro[1,4]dioxino[2, 3-f]quinolin-2-yl]methyl 4-bromobenzenesulfonate ester (0.18 g, 0.40 mmol), 4-benzofuran-2-yl-1,2,3,6-tetrahydropyridine (0.15 g, 0.75 mmol) and potassium carbonate (0.21 g, 1.5 mmol) in 3 mL of N,N-dimethylformamide was stirred under nitrogen at 60° C. for 24 hours. The mixture was partitioned between 250 mL each of water and ethyl acetate. The organic fraction was dried over magnesium sulfate, filtered and concentrated in vacuum. The residue was column chromatographed on 50 mL of silica gel using first 25% ethyl acetate in hexane and then 50% ethyl acetate in hexane as eluant. Combination and concentration of the product fractions gave 0.025 g of the S enantiomer of the title compound as a pale yellow solid, m.p. 149-150° C.

Elemental Analysis for: $C_{26}H_{24}N_2O_3.0.5\ H_2O$

Calc'd: C, 74.09; H, 5.98; N, 6.65

Found: C, 73.96; H, 5.89; N, 6.43

EXAMPLE 12

2-(4-Benzofuran-2-yl-piperidin-1-ylmethyl)-8-methyl-2,3-dihydro-[1,4]dioxino[2,3-f]quinoline A mixture of [(2R)-8-methyl-2,3-dihydro[1,4]dioxino[2, 3-f]quinolin-2-yl]methyl 4-bromobenzenesulfonate ester (0.18 g, 0.40 mmol), 4-benzofuran-2-yl-piperidine (0.103 g, 0.51 mmol) and potassium carbonate (0.21 g, 1.5 mmol) in 3 mL of N,N-dimethylformamide was stirred under nitrogen at room temperature for 3 days and then at 60° C. for 6 hours. The mixture was partitioned between 250 mL each of water and ethyl acetate. The organic fraction was dried over magnesium sulfate, filtered and concentrated in vacuum. The residue was column chromatographed on 50 mL of silica gel using first 25% ethyl acetate in hexane and then 50% ethyl acetate in hexane as eluant. Combination and concentration of the product fractions gave 0.060 g of the S enantiomer of the title compound as a pale yellow solid, m.p. 103-104° C.

Elemental Analysis for: $C_{26}H_{26}N_2O_3.0.25\ H_2O$

Calc'd: C, 74.53; H, 6.37; N, 6.69

Found: C, 74.52; H, 6.49; N, 6.63

Intermediate 26

4-(5-Chloro-benzo[b]thiophen-3-yl)-pyridine

To 3-bromo-5-chloro-benzo[b]thiophene (9.80 g, 39.6 mmol) was added pyridine-4-boronic acid (4.445 g, 36.2 mmol), $K_3PO_4$ (19.5 g, 91.9 mmol), 61 mL of 1,4-dioxane and 6 mL of water. The mixture was placed under house vacuum for several minutes and flushed with nitrogen. This was repeated 5 times. $Pd(dppf)Cl_2.CH_2Cl_2$ (2.71 g, 3.31 mmol), PdCl2 (0.0563 g, 0.318 mmol) and 1,1"-bis(diphenylphosphino)ferrocene (0.1747 g, 0.3151 mmol) were purged in the same way. The catalyst was added to the reaction flask which was purged with nitrogen 3 more times. The mixture was stirred (stir bar) at 80° C. for 22 hours. TLC showed little change. The mixture was mechanically stirred at 80° C. for 4 hours. The mixture was partitioned between water and ethyl acetate, filtered through Celite and the layers were separated. The organic layer was evaporated. The residue was dissolved in ethyl acetate, washed with water twice. Saturated brine was added the secondtime to separate.the layers more,quickly. The organic solution was dried over magnesium sulfate. Filtration and contration in vacuum gave 11.35 g of black oil. This was eluted from silica gel with a gradient of hexane and ethyl acetate to give 3.86 g of recovered starting material and 4.28 g of the title compound as light brown crystals, m.p. 90-91° C.

Elemental Analysis for: $C_{13}H_8CINS$

Calc'd: C, 63.54; H, 3.28; N, 5.70

Found: C, 63.19; H, 3.26; N, 5.46

EXAMPLE 13

2-[4-(5-Chloro-benzo[b]thiophen-3-yl)-3,6-dihydro-2H-pyridin-1-ylmethyl]-8- methyl-2,3-dihydro-[1,4]dioxino[2,3-f]quinoline To a mixture of [(2R)-8-methyl-2,3-dihydro[1,4]dioxino[2,3-f]quinolin-2-yl]methyl 4-bromobenzenesulfonate ester (0.92 g, 2.0 mmol) and 4-(5-chloro-benzo[b]thiophen-3-yl)-pyridine (0.50 g, 2.0 mmol) was added 8 mL of acetone. The mixture was refluxed for 4 hours, stirred at room temperature overnight and refluxed for 5 hours more. The solvent slowly evaporated and was replenished as needed. After standing at room temperature overnight some crystals had formed. To this was added 15 mL of methylethylketone. The mixture was refluxed overnight. TLC on silical gel showed starting material and no obvious product. The solvent was evaporated. The residue was stirred at 130° C. overnight. The thick mixture had solidified. It was broken up and crushed. To this was added 12 mL of ethanol. This heterogeneous mixture was stirred in an ice-bath. Sodium borohydride (0.12 g, 3.2 mmol) was added initially. A slight excess was added to insure consumption of the pyridinium salt. The reaction was allowed to stir and warm to room temperature overnight. The solvent was evaporated at reduced pressure. The residue was partitioned between ethyl acetate and water. The ethyl acetate layer was washed with water 3 times and dried over anhydrous magnesium sulfate. Filtration and concentration in vacuum gave 0.84 g of dark oil. This was chromatographed on silica gel with a gradient of ethyl acetate and hexane to give 0.29 g of the free base as an oil. This was dissolved in ethanol and added to a solution of oxalic acid dihydrate (0.0811 g, 0.643 mmol) in ethanol. Filtration gave 0.2659 g of the S enantiomer of the title compound as white oxalate, m.p. 203-207° C.

Elemental Analysis for: $C_{26}H_{23}CIN_2O_2S.C_2H_2O_4.\tfrac{2}{3}\ H_2O$

Calc'd: C,.59.52;H, 4.70; N, 4;96

Found: C, 59.59; H, 4.40; N, 4.74

EXAMPLE 14

2-(4-Benzoxazol-2-yl-piperidin-1-ylmethyl)-8-methyl-2,3-dihydro-[1,4]dioxino[2,3-f]quinoline A mixture of [(2R)-8-methyl-2,3-dihydro[1,4]dioxino[2,3-f]quinolin-2-yl]methyl 4-bromobenzenesulfonate ester (0.18 g, 0.40 mmol), 2-piperidin-4-yl-benzoxazole (0.121 g, 0.59 mmol) and potassium carbonate (0.21 g, 1.5 mmol) in 3 mL of N,N-dimethylformamide was stirred under nitrogen at room temperature for 3 days and then at 60 ° C. for 6 hours. The mixture was partitioned between 250 mL each of water and ethyl acetate. The organic fraction was dried over magnesium sulfate, filtered and concentrated in vacuum. The residue was column chromatographed on 50 mL of silica gel using first 50% ethyl acetate in hexane and then 75% ethyl acetate/hexane as eluant. Combination and concentration of the product fractions gave 0.040 g of the S enantiomer of the title compound as a dark beige solid, m.p. 128-130° C.

Elemental Analysis for: $C_{25}H_{25}N_3O_3.0.25\ H_2O$

Calc'd: C, 71.49; H, 6.12; N, 10.00

Found: C, 71.60; H, 6.06; N, 10.19

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be madewithoutdeparting from the spirit of the invention. It is, therefore, intended that the appended claims cover all such equivalent variations as fall within the true spirit and scope of the invention.

What is claimed is:

1. A compound of formula I:

wherein
R$^1$, R$^2$ and R$^3$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;
X and Y, taken together, form —NH—C(R$^8$)=CH—;
R$^8$ is hydrogen, halo, trifluoromethyl, pentafluoroethyl, or alkyl of 1 to 6 carbon atoms;
the dotted line represents an optional double bond;
Z is oxygen or sulfur;
Q is carbon or nitrogen; and
n is 0 or 1;
or a pharmaceutically acceptable salt thereof.

2. A compound according to claim 1, wherein Q is carbon and Z is sulfur.

3. A compound according to claim 1 having Formula Ib or a pharmaceutically acceptable salt thereof.

4. A compound according to claim 1, wherein R$^1$ is hydrogen, halo, cyano, trifluoromethyl, alkyl of 1 to 6 carbon atoms or alkoxy of 1 to 6 carbon atoms.

5. A compound according to claim 1, wherein R$^1$ is hydrogen, halo or alkoxy of 1 to 6 carbon atoms.

6. A compound according to claim 1, wherein R$^1$ is hydrogen.

7. A compound according to claim 1, wherein R$^2$ and R$^3$ are independently selected from hydrogen, hydroxy, halo, cyano, carboxamido, alkyl of 1 to 6 carbon atoms, or alkoxy of 1 to 6 carbon atoms.

8. A compound according to claim 1, wherein R$^2$ and R$^3$ are independently selected from hydrogen, cyano or halogen.

9. A compound according to claim 1, wherein R$^8$ is hydrogen, trifluoromethyl, pentafluoroethyl or alkyl of 1 to 6 carbon atoms.

10. A compound according to claim 1, wherein R$^8$ hydrogen, trifluoromethyl or alkyl of 1 to 3 carbon atoms.

11. A compound according to claim 1, wherein n is 0 and the dotted line represents a double bond.

12. A compound according to claim 1, wherein said compound is 2-(4-benzo[b]thiophen-3-yl-3,6-dihydro-2H-pyridin-1-ylmethyl)-2,3-dihydro-7H-[1,4]dioxino[2,3-e]indole or a pharmaceutically acceptable salt thereof.

13. A compound according to claim 1, wherein said compound is 2-[4-(5-fluoro-benzo[b]thiophen-3-yl)-3,6-dihydro-2H-pyridin-1-ylmethyl]-2,3-dihydro-7H-[1,4]dioxino[2,3-e]indole or a pharmaceutically acceptable salt thereof.

14. A compound according to claim 1, wherein said compound is the S enantiomer, substantially free of the R enantiomer of said compound.

15. A pharmaceutical composition, comprising:
an effective amount of a compound according to claim 1 or a pharmaceutically acceptable salt thereof; and
a pharmaceutically acceptable carrier or excipient.

16. A method of treating a subject suffering from a condition selected from depression, anxiety, panic disorder, post-traumatic stress disorder, premenstrual dysphoric disorder, attention deficit disorder, obsessive compulsive disorder, social anxiety disorder, generalized anxiety disorder, anorexia nervosa, bulimia nervosa, vasomotor flushing, cocaine and alcohol addiction, and premature ejaculation, comprising the step of:
administering to said subject suffering from said condition, a therapeutically effective amount of a compound according to claim 1 or a pharmaceutically acceptable salt thereof.

17. A method according to claim 16, wherein the condition is depression.

18. A method according to claim 16, wherein the condition is selected from the group consisting of obsessive compulsive disorder, panic attacks, generalized anxiety disorder, and social anxiety disorder.

* * * * *